US010300124B2

United States Patent
Milich et al.

(10) Patent No.: US 10,300,124 B2
(45) Date of Patent: May 28, 2019

(54) RODENT HEPADNAVIRUS CORES WITH REDUCED CARRIER-SPECIFIC ANTIGENICITY

(71) Applicant: VLP Biotech, Inc., San Diego, CA (US)

(72) Inventors: David R. Milich, Escondido, CA (US); David C. Whitacre, San Diego, CA (US)

(73) Assignee: VLP BIOTECH, INC., San Diego, CA (US)

( * ) Notice: Subject to any disclaimer, the term of this patent is extended or adjusted under 35 U.S.C. 154(b) by 0 days.

(21) Appl. No.: 14/774,108

(22) PCT Filed: Mar. 14, 2014

(86) PCT No.: PCT/US2014/029327
§ 371 (c)(1),
(2) Date: Sep. 9, 2015

(87) PCT Pub. No.: WO2014/144775
PCT Pub. Date: Sep. 18, 2014

(65) Prior Publication Data
US 2016/0022801 A1  Jan. 28, 2016

Related U.S. Application Data

(60) Provisional application No. 61/852,099, filed on Mar. 15, 2013.

(51) Int. Cl.
| | | |
|---|---|---|
| *A61K 39/12* | (2006.01) | |
| *A61K 39/015* | (2006.01) | |
| *A61K 39/29* | (2006.01) | |
| *C12N 7/00* | (2006.01) | |
| *A61K 39/07* | (2006.01) | |
| *A61K 39/155* | (2006.01) | |
| *A61K 39/385* | (2006.01) | |
| *A61K 39/00* | (2006.01) | |

(52) U.S. Cl.
CPC ............ *A61K 39/12* (2013.01); *A61K 39/015* (2013.01); *A61K 39/07* (2013.01); *A61K 39/155* (2013.01); *A61K 39/292* (2013.01); *A61K 39/385* (2013.01); *C12N 7/00* (2013.01); *A61K 2039/5258* (2013.01); *A61K 2039/55566* (2013.01); *C12N 2730/10023* (2013.01); *C12N 2730/10034* (2013.01); *C12N 2730/10043* (2013.01); *C12N 2730/10134* (2013.01); *C12N 2730/10143* (2013.01); *C12N 2740/16034* (2013.01); *C12N 2760/16134* (2013.01); *C12N 2760/18534* (2013.01)

(58) Field of Classification Search
None
See application file for complete search history.

(56) References Cited

U.S. PATENT DOCUMENTS

| | | |
|---|---|---|
| 6,231,864 B1 | 5/2001 | Birkett |
| 6,942,866 B2 | 9/2005 | Birkett |
| 7,144,712 B2 | 12/2006 | Milich et al. |
| 7,320,795 B2 | 1/2008 | Milich et al. |
| 7,811,576 B2 | 10/2010 | Milich et al. |
| 7,883,843 B2 | 2/2011 | Milich et al. |
| 2005/0025781 A1* | 2/2005 | Milich ............... A61K 39/015 424/189.1 |
| 2005/0208068 A1 | 9/2005 | Milich et al. |
| 2011/0206724 A1 | 8/2011 | Milich et al. |
| 2016/0039883 A1 | 2/2016 | Milich et al. |

FOREIGN PATENT DOCUMENTS

| | | |
|---|---|---|
| WO | 2005/011571 A2 | 2/2005 |
| WO | 2014/144756 A1 | 9/2014 |

OTHER PUBLICATIONS

NCBI Reference Sequence NC_004107.1, 2009, Woodchuck Hepatitis Virus Complete Genome.*
NCBI Reference Sequence NP_671816.1, 2009, Core Protein of Woodchuck Hepatitis Virus.*
Extended European Search Report (includes Supplementary European Search Report and Search Opinion) received for European Patent Application No. 14764250.8, dated Dec. 9, 2016, 12 pages.
UniProt Database Accession No. Q0GBW8, Available online at <http://www.uniprot.org/uniprot/Q0GBW8.txt>, Oct. 3, 2006, 2 pages.
Bang et al., "Effect of Mutating the two Cysteines Required for HBE Antigenicity on Hepatitis B Virus DNA Replication and Virion Secretion", Virology, vol. 332, 2005, pp. 216-224.
Belnap et al., "Diversity of Core Antigen Epitopes of Hepatitis B virus", Proc Natl Acad Sci USA, vol. 100, No. 19, 2003, 10884-10889.
Bichko et al., "Epitopes Recognized by Antibodies to Denatured Core Protein of Hepatitis B Virus", Molecular Immunology, vol. 30, No. 3, 1993, pp. 221-231.
Billaud et al., "Advantages to the Use of Rodent Hepadnavirus Core Proteins as Vaccine Platforms", Vaccine, vol. 25, 2007, pp. 1593-1606.
Billaud et al., "Combinatorial Approach to Hepadnavirus-Like Particle Vaccine Design", J Virol, vol. 79, No. 21, 2005, pp. 13656-13666.
Billaud et al., "Comparative Antigenicity and Immunogenicity of Hepadnavirus Core Proteins", J Virol, vol. 79, No. 21, 2005, pp. 13641-13655.

(Continued)

*Primary Examiner* — Stacy B Chen
(74) *Attorney, Agent, or Firm* — Morrison & Foerster LLP

(57) ABSTRACT

The present disclosure generally relates to hepadnavirus core antigens in which one or more endogenous b cell epitopes have been effectively removed. More specifically, the present disclosure relates to rodent hepadnavirus cores modified to diminish the antibody response to the core so as to enhance the antibody response to heterologous polypeptides included therein.

17 Claims, 6 Drawing Sheets

Specification includes a Sequence Listing.

(56) References Cited

OTHER PUBLICATIONS

Brown et al., "Foreign Epitopes in Immunodominant Regions of Hepatitis B Core Particles are Highly Immunogenic and Conformationally Restricted", Vaccine, vol. 9, No. 8, 1991, pp. 591-601.
Cohen et al.,"Sequence Comparison of Woodchuck Hepatitis Virus Replicative forms Shows Conservation of the Genome", Virology, vol. 162, No. 1, 1988, pp. 12-20.
Harris et al., "Epitope Diversity of Hepatitis B Virus Capsids: Quasi-Equivalent Variations in Spike Epitopes and Binding of Different Antibodies to the same Epitope", J Mol Bio, vol. 355, No. 3, 2006, pp. 562-576.
International Preliminary Report on Patentability received for PCT Patent Application No. PCT/US2014/029327, dated Sep. 24, 2015, 7 pages.
International Search Report and Written Opinion received for PCT Patent Application No. PCT/US2014/029327 dated Nov. 28, 2014, 11 pages.
Invitation to Pay Additional Fees received for PCT Patent Application No. PCT/US2014/029327, dated Aug. 27, 2014, 2 pages.
Isaguliants et al.,"Specificity of Humoral and Cellular Immune Response against Recombinant Particles of Nucleocapsid Protein of Human Hepatitis B Virus in Rabbits", Biochemistry (Moscow) vol. 63, No. 5, 1998, pp. 551-558. (abstract only).
Lucchese et al., "How a Single Amino Acid Change may alter the Immunological Information of a Peptide", Frontiers in Bioscience, vol. 4, 2012, pp. 1843-1852.
Milich et al., "Conversion of Poorly Immunogenic Malaria Repeat Sequences into a Highly Immunogenic Vaccine Candidate", Vaccine, vol. 20, 2002, pp. 771-788.
Nassal et al., "An Intramolecular Disulfide Bridge between Cys-7 and Cys61 Determines the Structure of the Secretory Core Gene Product (E Antigen) of Hepatitis B Virus", J Virol, vol. 67, No. 7., 1993, pp. 4307-4315.
Nassal, "Conserved Cysteines of the Hepatitis B Virus Core Protein are not Required for Assembly of Replication-Competent Core Particles nor for their Envelopment", Virology, vol. 190, No. 1, 1992, pp. 499-505.

Partial Supplementary European Search Report received for European Patent Application No. 14764250.8, dated Jul. 29, 2016, 8 pages.
Pushko et al., "Identification of Hepatitis B Virus Core Protein Regions Exposed or Internalized at the Surface of HBcAg Particles by Scanning With Monoclonal Antibodies", Virology, vol. 202, No. 2, 1994, pp. 912-920.
Renjifo et al., "Carrier-Induced, Hapten-Specific Suppression: a Problem of Antigen Presentation?", J Immunol, vol. 161, 1998, pp. 702-706.
Roseman et al., "Structures of Hepatitis B Virus Cores Presenting a Model Epitope and Their Complexes with Antibodies", J Mol Biol, vol. 423, 2012, pp. 63-78.
Schickli et al., "Palivizumab Epitope-Displaying Virus-like Particles Protect Rodents from RSV Challenge", J Clin Invest, vol. 125, No. 4, 2015, pp. 1637-1647.
Schodel et al., "Immunity to Malaria Elicited by Hybrid Hepatitis B Virus Core Particles Carrying Circumsporozoite Protein Epitopes", J Exp Med, vol. 180, 1994, pp. 1037-1046.
Schodel et al., "The Position of Heterologous Epitopes Inserted in Hepatitis B Virus Core Particles Determines Their Immunogenicity", J Virol, vol. 66, No. 01, 1992, pp. 106-114.
Wasenauer et al., "Relevance of Cysteine Residues for Biosynthesis and Antigenicity of Human Hepatitis B Virus E Protein", J Virol, vol. 67, No. 3, 1993, pp. 1315-1321.
Whitacre et al., "Use of Hepadnavirus Core Proteins as Vaccine Platforms", Expert Review of Vaccines, vol. 8, No. 11, 2009, pp. 1565-1573.
Whitcare et al., "P. Falciparum and P. Vivax Epitope-Focused VLPS Elicit Sterile Immunity to Blood Stage Infections", PLoS ONE, vol. 10, 2015, pp. 1-22.
Zhang et al., "A Conserved Linear B-Cell Epitope at the N-Terminal Region of Woodchuck Hepatitis Virus Core Protein (Whcag)", Journal of Virological Methods, vol. 135, No. 1, 2006, pp. 17-25.
Zheng et al., "Characterization of Complex B Cell Epitopes on Woodchuck Hepatitis Virus Surface Antigens by Using Plasmids Encoding Chimeric Proteins and DNA Immunization", Virology, vol. 294, 2002, pp. 342-353.

* cited by examiner

```
        1         10         20         30         40         50         60
WHcAg   MDIDPYKEFG SSYQLLNFLP LDFFPDLNAL VDTATALYEE ELTGREHCSP HHTAIRQALV
GScAg   MDIDPYKEFG SSYQLLNFLP LDFFPDLNAL VDTAAALYEE ELTGREHCSP HHTAIRQALV
AGScAg  MDIDPYKEFG SSYQLLNFLP LDFFPELNAL VDTATALYEE ELTGREHCSP HHTAIRQALV
HBcAg   MDIDPYKEFG ATVELLSFLP SDFFPSVRDL LDNASALYRE ALESPEHCSP HHTALRQAIL
Δ2      .......... .......... A....AAAV.A .......... .......... ..........
Δ3      .......... .......... .......... .......... .......... ..........
Δ4      .......... .......... .......... .......... .......... ..........
Δ5      .......... .......... .......... .......... .......... ..........
Δ6      .......... .......... .......... .......... .......... ..........
Δ7      .......... .......... .......... .......... .......... ..........

70         80         90        100        110        120
WHcAg   CWDELTKLIA WMSSNITSEQ VRTIIVNHVN DTWGLKVRQS LWFHLSCLTF GQHTVQEFLV
GScAg   CWEELTRLIT WMSEN-TIEE VRRIIVDHVN NTWGLKVRQT LWFHLSCLTF GQHTVQEFLV
AGScAg  CWEELTRLIA WMSANINSEE VRRVIVAHVN DTWGLKVRQN LWFHLSCLTF GQHTVQEFLV
HBcAg   CWGELMTLAT WVGGNLEDPI SRDLVVSYVN TNMGLKFRQL LWFHISCLTF GRETVIEYLV
Δ2      .......... .......... .......... .......... .......... ..........
Δ3      .......... .......... .......... .......... .......... ..........
Δ4      S......... .......... .......... .......... .......... ..........
Δ5      .XXXXXXXXX XXXXXXXXXX XXXXXXX... .......... .......... ..........
Δ6      .......... .......... .......... .......... .......... ..........
Δ7      .......... ....AAAAAA AAA....... .......... .......... ..........

130        140        150        160        170        180
WHcAg   SFGVWIRTPA PYRPPNAPIL STLPEHTVIR RRGGARASRS PRRRTPSPRR RRSQSPRRRR
GScAg   SFGVWIRTPA PYRPPNAPIL STLPEHTVIR RRGGSRAARS PRRRTPSPRR RRSQSPRRRR
AGScAg  SFGVRIRTPA PYRPPNAPIL STLPEHTVIR RRGSARVVRS PRRRTPSPRR RRSQSPRRRR
HBcAg   SFGVWIRTPP AYRPPNAPIL STLPETTVVR RRG------RS PRRRTPSPRR RRSQSPRRRR
Δ2      .......... .......... .......... .......... .......... ..........
Δ3      .......... ...PP..... .......... .......... .......... ..........
Δ4      .......... .......... .......... .......... .......... ..........
Δ5      .......... .......... .......... .......... .......... ..........
Δ6      .......... .......... .A.AA...A..A. .AAA....AA A....AAAA
Δ7      .......... .......... .......... .......... .......... ..........

WHcAg   SQSPSANC 188
GScAg   SQSPASNC 187
AGScAg  -QSPASNC 187
HBcAg   SQSRESQC 183
Δ2      ........
Δ3      ........
Δ4      ........
Δ5      ........
Δ6      ........
Δ7      ........
```

Figure 1A

Fusion Protein Expression
VLP Assembly
VLP Yield (> 75 mg/L)
VLP Stability (> 65°C)

↓

Antigenicity Testing
anti-insert Ab binding
VLP competition w/ Ag for Ab binding

↓

VLP Immune Serum Testing
Pathogen Neutralization

↓

Immunogenicity Testing
Ab production to insert
Ab production to Ag
IgG isotype distribution

↓

Pathogen Challenge
Reduced pathogen titers
Disease protection

Figure 1C

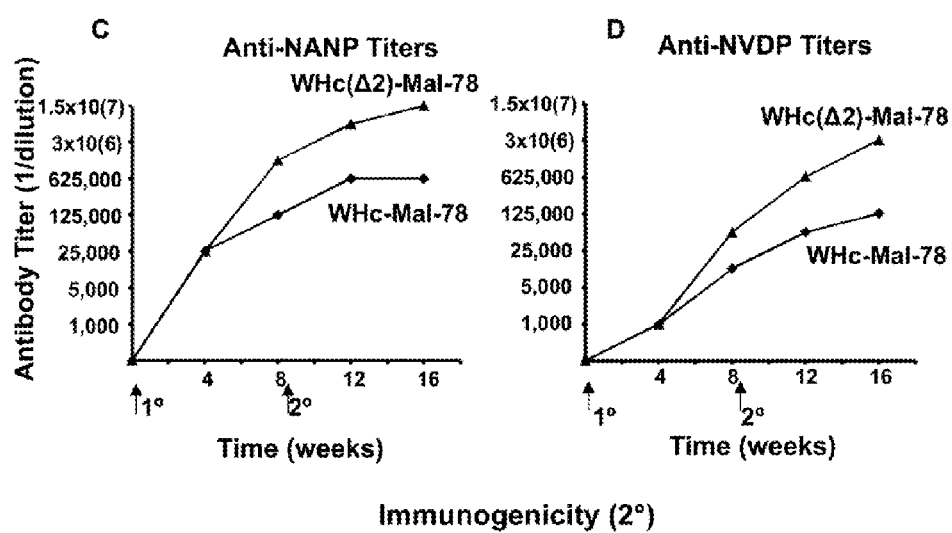
Figure 3 (contd.)

SEQUENCE LISTING

<160> NUMBER OF SEQ ID NOS: 32

<210> SEQ ID NO 1
<211> LENGTH: 188
<212> TYPE: PRT
<213> ORGANISM: Woodchuck hepatitis virus

<400> SEQUENCE: 1

```
Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Arg Gly Gly Ala Arg Ala Ser Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Pro Ser Ala Asn Cys
            180                 185
```

<210> SEQ ID NO 2
<211> LENGTH: 188
<212> TYPE: PRT
<213> ORGANISM: Artificial Sequence
<220> FEATURE:
<223> OTHER INFORMATION: Synthesized Construct

<400> SEQUENCE: 2

Met Asp Ile Asp Pro Tyr Lys Glu Phe Gly Ser Ser Tyr Gln Leu Leu
1               5                   10                  15

Asn Phe Leu Pro Ala Asp Phe Phe Pro Ala Ala Val Leu Ala Asp
            20                  25                  30

Thr Ala Thr Ala Leu Tyr Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Arg Gly Gly Ala Arg Ala Ser Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Pro Ser Ala Asn Cys
            180                 185

<210> SEQ ID NO 3
<211> LENGTH: 188
<212> TYPE: PRT
<213> ORGANISM: Artificial Sequence
<220> FEATURE:
<223> OTHER INFORMATION: Synthesized Construct

<400> SEQUENCE: 3

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Pro Pro Ile Leu Ser Thr Leu Pro
    130                 135                 140

Glu His Thr Val Ile Arg Arg Arg Gly Gly Ala Arg Ala Ser Arg Ser
145                 150                 155                 160

```
Pro Arg Arg Arg Thr Pro Ser Pro Arg Arg Arg Ser Gln Ser Pro
                165                 170                 175

Arg Arg Arg Arg Ser Gln Ser Pro Ser Ala Asn Cys
            180                 185

<210> SEQ ID NO 4
<211> LENGTH: 188
<212> TYPE: PRT
<213> ORGANISM: Artificial Sequence
<220> FEATURE:
<223> OTHER INFORMATION: Synthesized Construct

<400> SEQUENCE: 4

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
                20                  25                  30

Thr Ala Thr Ala Leu Tyr Glu Glu Glu Leu Thr Gly Arg Glu His Cys
            35                  40                  45

Ser Pro His His Thr Ala Ile Arg Gln Ala Leu Val Ser Trp Asp Glu
        50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
                100                 105                 110

His Thr Val Gln Glu Phe Leu Val Ser Phe Gly Val Trp Ile Arg Thr
            115                 120                 125

Pro Ala Pro Tyr Arg Pro Pro Asn Ala Pro Ile Leu Ser Thr Leu Pro
        130                 135                 140

Glu His Thr Val Ile Arg Arg Gly Gly Ala Arg Ala Ser Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Pro Ser Ala Asn Cys
            180                 185

<210> SEQ ID NO 5
<211> LENGTH: 188
<212> TYPE: PRT
<213> ORGANISM: Artificial Sequence
<220> FEATURE:
<223> OTHER INFORMATION: Synthesized Construct
<220> FEATURE:
<221> NAME/KEY: VARIANT
<222> LOCATION: 62, 63, 64, 65, 66, 67, 68, 69, 70, 71, 72, 73, 74, 75,
      76, 77, 78, 79, 80, 81, 82, 83, 84, 85, 86, 87
<223> OTHER INFORMATION: Xaa = Any Amino Acid

<400> SEQUENCE: 5

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
                20                  25                  30

Thr Ala Thr Ala Leu Tyr Glu Glu Glu Leu Thr Gly Arg Glu His Cys
            35                  40                  45

Ser Pro His His Thr Ala Ile Arg Gln Ala Leu Val Cys Xaa Xaa Xaa
        50                  55                  60
```

```
Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
            115                 120                 125

Pro Ala Pro Tyr Arg Pro Pro Asn Ala Pro Ile Leu Ser Thr Leu Pro
            130                 135                 140

Glu His Thr Val Ile Arg Arg Gly Gly Ala Arg Ala Ser Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Pro Ser Ala Asn Cys
            180                 185
```

<210> SEQ ID NO 6
<211> LENGTH: 188
<212> TYPE: PRT
<213> ORGANISM: Artificial Sequence
<220> FEATURE:
<223> OTHER INFORMATION: Synthesized Construct

<400> SEQUENCE: 6

```
Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
            115                 120                 125

Pro Ala Pro Tyr Arg Pro Pro Asn Ala Pro Ile Leu Ser Thr Leu Pro
            130                 135                 140

Glu His Thr Val Ile Ala Ala Gly Gly Ala Ala Ala Ser Ala Ser
145                 150                 155                 160

Pro Ala Ala Ala Thr Pro Ser Pro Ala Ala Ala Arg Ser Gln Ser Pro
                165                 170                 175

Ala Ala Ala Ala Ser Gln Ser Pro Ser Ala Asn Cys
            180                 185
```

<210> SEQ ID NO 7
<211> LENGTH: 188
<212> TYPE: PRT
<213> ORGANISM: Artificial Sequence
<220> FEATURE:
<223> OTHER INFORMATION: Synthesized Construct

<400> SEQUENCE: 7

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ala Ala Ala Ala Ala Ala
65                  70                  75                  80

Ala Ala Ala Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Arg Gly Gly Ala Arg Ala Ser Arg Ser
145                 150                 155                 160

Pro Arg Arg Arg Thr Pro Ser Pro Arg Arg Arg Ser Gln Ser Pro
            165                 170                 175

Arg Arg Arg Arg Ser Gln Ser Pro Ser Ala Asn Cys
            180                 185

<210> SEQ ID NO 8
<211> LENGTH: 187
<212> TYPE: PRT
<213> ORGANISM: Ground Squirrel Hepatitis Virus

<400> SEQUENCE: 8

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Ala Ala Leu Tyr Glu Glu Leu Thr Gly Arg Glu His Cys
        35                  40                  45

Ser Pro His His Thr Ala Ile Arg Gln Ala Leu Val Cys Trp Glu Glu
    50                  55                  60

Leu Thr Arg Leu Ile Thr Trp Met Ser Glu Asn Thr Thr Glu Glu Val
65                  70                  75                  80

Arg Arg Ile Ile Val Asp His Val Asn Asp Thr Trp Gly Leu Lys Val
                85                  90                  95

Arg Gln Thr Leu Trp Phe His Leu Ser Cys Leu Thr Phe Gly Gln His
            100                 105                 110

Thr Val Gln Glu Phe Leu Val Ser Phe Gly Val Trp Ile Arg Thr Pro
        115                 120                 125

Ala Pro Tyr Arg Pro Pro Asn Ala Pro Ile Leu Ser Thr Leu Pro Glu
    130                 135                 140

His Thr Val Ile Arg Arg Arg Gly Gly Ser Arg Ala Ala Arg Ser Pro
145                 150                 155                 160

```
Arg Arg Arg Thr Pro Ser Pro Arg Arg Arg Ser Gln Ser Pro Arg
            165                 170                 175

Arg Arg Arg Ser Gln Ser Pro Ala Ser Asn Cys
            180                 185

<210> SEQ ID NO 9
<211> LENGTH: 187
<212> TYPE: PRT
<213> ORGANISM: Arctic Ground Squirrel Hepatitis Virus

<400> SEQUENCE: 9

Met Asp Ile Asp Pro Tyr Lys Glu Phe Gly Ser Ser Tyr Gln Leu Leu
1               5                   10                  15

Asn Phe Leu Pro Leu Asp Phe Phe Pro Glu Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Glu Glu
    50                  55                  60

Leu Thr Arg Leu Ile Ala Trp Met Ser Ala Asn Ile Asn Ser Glu Glu
65                  70                  75                  80

Val Arg Arg Val Ile Val Ala His Val Asn Asp Thr Trp Gly Leu Lys
                85                  90                  95

Val Arg Gln Asn Leu Trp Phe His Leu Ser Cys Leu Thr Phe Gly Gln
            100                 105                 110

His Thr Val Gln Glu Phe Leu Val Ser Phe Gly Val Arg Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Arg Gly Ser Ala Arg Val Val Arg Ser
145                 150                 155                 160

Pro Arg Arg Arg Thr Pro Ser Pro Arg Arg Arg Ser Gln Ser Pro
                165                 170                 175

Arg Arg Arg Arg Gln Ser Pro Ala Ser Asn Cys
            180                 185

<210> SEQ ID NO 10
<211> LENGTH: 183
<212> TYPE: PRT
<213> ORGANISM: Human Hepatitis B Virus

<400> SEQUENCE: 10

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110
```

```
Glu Thr Val Ile Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Gly Arg Ser Pro Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180

<210> SEQ ID NO 11
<211> LENGTH: 149
<212> TYPE: PRT
<213> ORGANISM: Artificial Sequence
<220> FEATURE:
<223> OTHER INFORMATION: Synthesized Construct

<400> SEQUENCE: 11

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile
145

<210> SEQ ID NO 12
<211> LENGTH: 188
<212> TYPE: PRT
<213> ORGANISM: Artificial Sequence
<220> FEATURE:
<223> OTHER INFORMATION: Synthesized Construct
<220> FEATURE:
<221> NAME/KEY: VARIANT
<222> LOCATION: (1)...(188)
<223> OTHER INFORMATION: Xaa = Any Amino Acid or Absent

<400> SEQUENCE: 12

Met Asp Ile Asp Pro Tyr Lys Glu Phe Gly Ser Ser Tyr Gln Leu Leu
1               5                   10                  15

Asn Phe Leu Pro Xaa Asp Phe Phe Pro Xaa Xaa Xaa Leu Xaa Asp
            20                  25                  30

Thr Ala Thr Ala Leu Tyr Glu Glu Leu Thr Gly Arg Glu His Cys
        35                  40                  45
```

Ser Pro His His Thr Ala Ile Arg Gln Ala Leu Val Xaa Xaa Xaa Xaa
            50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa His Val Asn Asp Thr Trp Gly Leu Lys
                    85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
            115                 120                 125

Pro Ala Pro Tyr Arg Pro Pro Xaa Xaa Pro Ile Leu Ser Thr Leu Pro
            130                 135                 140

Glu His Thr Val Ile Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa
            180                 185

<210> SEQ ID NO 13
<211> LENGTH: 188
<212> TYPE: PRT
<213> ORGANISM: Artificial Sequence
<220> FEATURE:
<223> OTHER INFORMATION: Synthesized Construct
<220> FEATURE:
<221> NAME/KEY: VARIANT
<222> LOCATION: (1)...(188)
<223> OTHER INFORMATION: Xaa = Any Amino Acid or Absent

<400> SEQUENCE: 13

Met Asp Ile Asp Pro Tyr Lys Glu Phe Gly Ser Ser Tyr Gln Leu Leu
1               5                   10                  15

Asn Phe Leu Pro Xaa Asp Phe Phe Pro Xaa Xaa Xaa Xaa Leu Xaa Asp
            20                  25                  30

Thr Ala Thr Ala Leu Tyr Glu Glu Leu Thr Gly Arg Glu His Cys
            35                  40                  45

Ser Pro His His Thr Ala Ile Arg Gln Ala Leu Val Xaa Xaa Xaa Xaa
            50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa His Val Asn Asp Thr Trp Gly Leu Lys
                    85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
            115                 120                 125

Pro Ala Pro Tyr Arg Pro Pro Xaa Xaa Pro Ile Leu Ser Thr Leu Pro
            130                 135                 140

Glu His Thr Val Ile Xaa Xaa Xaa Gly Gly Ala Xaa Ala Ser Xaa Ser
145                 150                 155                 160

Pro Xaa Xaa Xaa Thr Pro Ser Pro Xaa Xaa Xaa Arg Ser Gln Ser Pro
                165                 170                 175

Xaa Xaa Xaa Xaa Ser Gln Ser Pro Ser Ala Asn Cys
            180                 185

```
<210> SEQ ID NO 14
<211> LENGTH: 20
<212> TYPE: PRT
<213> ORGANISM: Artificial Sequence
<220> FEATURE:
<223> OTHER INFORMATION: Synthesized Construct

<400> SEQUENCE: 14

Asn Ala Asn Pro Asn Val Asp Pro Asn Ala Asn Pro Asn Ala Asn Pro
1               5                   10                  15

Asn Ala Asn Pro
            20

<210> SEQ ID NO 15
<211> LENGTH: 24
<212> TYPE: PRT
<213> ORGANISM: Artificial Sequence
<220> FEATURE:
<223> OTHER INFORMATION: Synthesized Construct

<400> SEQUENCE: 15

Asn Ser Glu Leu Leu Ser Leu Ile Asn Asp Met Pro Ile Thr Asn Asp
1               5                   10                  15

Gln Lys Lys Leu Met Ser Asn Asn
            20

<210> SEQ ID NO 16
<211> LENGTH: 3323
<212> TYPE: DNA
<213> ORGANISM: Woodchuck hepatitis virus

<400> SEQUENCE: 16
aattcgggac ataccacgtg gtttagttcc gcctcaaact ccaacaaatc gagatcaagg      60
gagaaagcct actcctccaa ctccacctct aagagatact cacccccact taactatgaa    120
aaatcagact tttcatctcc aggggttcgt agacggatta cgagacttga caacaacgga    180
acgccaacac aatgcctatg agatcccttt tacaacacta gccctgcgg ttcctactgt     240 atccaccata ttgtctcctc cctcgacgac tggggaccct gcactgtcac cggagatgtc    300
accatcaagt ctcctaggac tcctcgcagg attacaggtg gtgtatttct tgtggacaaa    360
aatcctaaca atagctcaga atctagattg gtggtggact tctctcagtt ttccagggg     420 cataccagag tgcactggcc aaaattcgca gttccaaact tgcaaacact tgccaacctc    480
ctgtccacca acttgcaatg ctttcgttg gatgtatctg cggcgtttta tcatatacct     540
attagtcctg ctgctgtgcc tcatcttctt gttggttctc ctggactgga aaggtttaat    600
acctgtctgt cctcttcaac ccacaacaga acaacagtc aattgcagac aatgcacaat    660
ctctgcacaa gacatgtata ctcctcctta ctgttgttgt ttaaaaccta cggcaggaaa    720
ttgcacttgt tggcccatcc cttcatcatg ggctttagga aattacctat gggagtgggc    780
cttagcccgt ttctcttggc tcaatttact agtgcccttg cttcaatggt taggaggaat    840
ttccctcatt gcgtggtttt tgcttatatg gatgatttgg ttttgggggc ccgcacttct    900
gagcatctta ccgccattta ttcccatatt tgttctgtt ttcttgattt gggtatacat     960
ttgaatgtca ataaaacaaa atggtgggc aatcatctac atttcatggg atatgtgatt   1020
actagttcag gtgtattgcc acaagacaaa catgttaaga aatttcccg ttatttgcgc    1080 tctgttcctt taatcaacc tctggattac aaaatttgtg aaagattgac tggtattctt    1140
aactatgttg ctccttttac gctatgtgga tacgctgctt aatgcctttt gtatcatgct    1200
```

-continued

| | |
|---|---|
| attacttccc gtacggcttt cattttctcc tccttgtata aatcctggtt gctgtctctt | 1260 |
| tatgaggagt tgtggcccgt tgtcaggcaa cgtggcgtgg tgtgcactgt gtttgctgac | 1320 |
| gcaaccccca ctggttgggg cattgccacc acctatcaac tcctttccgg gactttcgct | 1380 |
| ttcccctcc ctattgccac ggcggaactc attgccgcct gccttgcccg ctgctggaca | 1440 |
| ggggctcggc tgttgggcac tgacaattcc gtggtgttgt cggggaagct gacgtccttt | 1500 |
| ccatggctgc tcgcctgtgt tgccaactgg attctgcgcg ggacgtcctt ctgctacgtc | 1560 |
| ccttcggccc tcaatccagc ggaccttcct tcccgcggcc tgctgccggt tctgcggcct | 1620 |
| cttccgcgtc ttcgccttcg ccctcagacg agtcggatct ccctttgggc cgcctccccg | 1680 |
| cctgtttcgc ctcggcgtcc ggtccgtgtt gcttggtctt cacctgtgca gaattgcgaa | 1740 |
| ccatggattc caccgtgaac tttgtctcct ggcatgcaaa tcgtcaactt ggcatgccaa | 1800 |
| gtaaggacct ttggactcct tatataaaag atcaattatt aactaaatgg gaggagggca | 1860 |
| gcattgatcc tagattatca atatttgtat taggaggctg taggcataaa tgcatgcgac | 1920 |
| ttctgtaacc atgtatcttt ttcacctgtg ccttgttttt gcctgtgttc catgtcctac | 1980 |
| ttttcaagcc tccaagctgt gccttggatg gctttgggc atggacatag atccctataa | 2040 |
| agaatttggt tcatcttatc agttgttgaa ttttcttcct ttggacttct ttcctgacct | 2100 |
| taatgctttg gtggacactg ctactgcctt gtatgaagaa gagctaacag gtagggaaca | 2160 |
| ttgctctccg caccatacag ctattagaca agctttagta tgctgggatg aattaactaa | 2220 |
| attgatagct tggatgagct ctaacataac ttctgaacaa gtaagaacaa tcatagtaaa | 2280 |
| tcatgtcaat gatacctggg gacttaaggt gagacaaagt ttatggtttc atttgtcatg | 2340 |
| tctcactttt ggacaacata cagttcaaga attttttagta agttttggag tatggatcag | 2400 |
| aactccagct ccatatagac ctcctaatgc acccattctc tcgactcttc cggaacatac | 2460 |
| agtcattagg agaagaggag gtgcaagagc ttctaggtcc cccagaagac gcactccctc | 2520 |
| tcctcgcagg agaagatctc aatcaccgcg tcgcagacgc tctcaatctc catctgccaa | 2580 |
| ctgctgatct tcaatgggta cataaaacta atgctattac aggtctttac tctaaccaag | 2640 |
| ctgctcagtt caatccgcat tggattcaac ctgagtttcc tgaacttcat ttacataatg | 2700 |
| atttaattca aaaattgcaa cagtattttg gtcctttgac tataaatgaa aagagaaaat | 2760 |
| tgcaattaaa ttttcctgcc agattttcc ccaaagctac taaatatttc cctttaatta | 2820 |
| aaggcataaa aaacaattat cctaattttg ctttagaaca tttctttgct accgcaaatt | 2880 |
| atttgtggac tttatgggaa gctggaattt tgtatttaag gaagaatcaa acaactttga | 2940 |
| cttttaaagg taaccatat tcttgggaac acagacagct agtgcaacat aatgggcaac | 3000 |
| aacataaaag tcaccttcaa tccagacaaa atagcagcat ggtggcctgc agtgggcact | 3060 |
| tattacacaa ccacttatcc tcagaatcag tcagtgtttc aaccaggaat ttatcaaaca | 3120 |
| acatctctga taaatcccaa aaatcaacaa gaactggact ctgttcttat aaacagatac | 3180 |
| aaacagatag actggaacac ttggcaagga tttcctgtgg atcaaaaatt accattggtc | 3240 |
| agcagggatc ctcccccaaa accttatata aatcaatcag ctcaaacttt cgaaatcaaa | 3300 |
| cctgggccta aatagttcc cgg | 3323 |

<210> SEQ ID NO 17
<211> LENGTH: 65
<212> TYPE: PRT
<213> ORGANISM: Artificial Sequence

```
<220> FEATURE:
<223> OTHER INFORMATION: Synthesized Construct
<220> FEATURE:
<221> NAME/KEY: VARIANT
<222> LOCATION: (5)...(64)
<223> OTHER INFORMATION: Xaa = Any Amino Acid and up to 60 of them can
      be present or absent

<400> SEQUENCE: 17

Gly Ile Leu Glu Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Leu
65

<210> SEQ ID NO 18
<211> LENGTH: 4
<212> TYPE: PRT
<213> ORGANISM: Artificial Sequence
<220> FEATURE:
<223> OTHER INFORMATION: Synthesized Construct

<400> SEQUENCE: 18

Trp Leu Trp Gly
1

<210> SEQ ID NO 19
<211> LENGTH: 12
<212> TYPE: PRT
<213> ORGANISM: Artificial Sequence
<220> FEATURE:
<223> OTHER INFORMATION: Synthesized Construct

<400> SEQUENCE: 19

Pro Pro Ala Tyr Arg Pro Pro Asn Ala Pro Ile Leu
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthesized Construct

<400> SEQUENCE: 20

Ala Pro Ala Tyr Arg Pro Pro Asn Ala Pro Ile Leu
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthesized Construct

<400> SEQUENCE: 21

Pro Ala Ala Tyr Arg Pro Pro Asn Ala Pro Ile Leu
1               5                   10
```

```
<210> SEQ ID NO 22
<211> LENGTH: 12
<212> TYPE: PRT
<213> ORGANISM: Artificial Sequence
<220> FEATURE:
<223> OTHER INFORMATION: Synthesized Construct

<400> SEQUENCE: 22

Pro Pro Phe Tyr Arg Pro Pro Asn Ala Pro Ile Leu
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthesized Construct

<400> SEQUENCE: 23

Pro Pro Ala Ala Arg Pro Pro Asn Ala Pro Ile Leu
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthesized Construct

<400> SEQUENCE: 24

Pro Pro Ala Tyr Ala Pro Pro Asn Ala Pro Ile Leu
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthesized Construct

<400> SEQUENCE: 25

Pro Pro Ala Tyr Arg Ala Pro Asn Ala Pro Ile Leu
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthesized Construct

<400> SEQUENCE: 26

Pro Pro Ala Tyr Arg Pro Ala Asn Ala Pro Ile Leu
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthesized Construct

<400> SEQUENCE: 27

Pro Pro Ala Tyr Arg Pro Pro Ala Ala Pro Ile Leu
1               5                   10
```

```
<210> SEQ ID NO 28
<211> LENGTH: 12
<212> TYPE: PRT
<213> ORGANISM: Artificial Sequence
<220> FEATURE:
<223> OTHER INFORMATION: Synthesized Construct

<400> SEQUENCE: 28

Pro Pro Ala Tyr Arg Pro Pro Asn Phe Pro Ile Leu
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthesized Construct

<400> SEQUENCE: 29

Pro Pro Ala Tyr Arg Pro Pro Asn Ala Ala Ile Leu
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthesized Construct

<400> SEQUENCE: 30

Pro Pro Ala Tyr Arg Pro Pro Asn Ala Pro Ala Leu
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthesized Construct

<400> SEQUENCE: 31

Pro Pro Ala Tyr Arg Pro Pro Asn Ala Pro Ile Ala
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthesized Construct

<400> SEQUENCE: 32

Pro Pro Ala Tyr Arg Pro Pro Pro Pro Pro Ile Leu
1               5                   10
```

RODENT HEPADNAVIRUS CORES WITH REDUCED CARRIER-SPECIFIC ANTIGENICITY

CROSS-REFERENCE TO RELATED APPLICATIONS

This application is a U.S. National Stage of PCT/US2014/029327, filed Mar. 14, 2014, which claims benefit of U.S. Provisional Application No. 61/852,099, filed Mar. 15, 2013, which are hereby incorporated by reference in their entirety.

STATEMENT REGARDING FEDERALLY SPONSORED RESEARCH

This invention was made with government support under Grant Nos. 2R44AI088919 and 5RO1AI082740 both awarded by the National Institute of Allergy and Infectious Diseases, of the National Institutes of Health. The government has certain rights in the invention.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 720222000100SeqList.txt, date recorded: Sep. 1, 2015, size: 369 KB).

FIELD

The present disclosure generally relates to rodent hepadnavirus core antigens in which one or more endogenous B cell epitopes have been effectively removed. More specifically, the present disclosure relates to rodent hepadnavirus cores modified to diminish the antibody response to the core so as to enhance the antibody response to heterologous polypeptides included therein.

BACKGROUND

Hepadnavirus core antigens have been developed as a vaccine carrier platform (Billaud et al., J Virol, 79:13656-13666, 2005, and as a drug delivery vehicle (Beterams et al., FEBS Lett, 481:169-176, 2000; and Lee and Tan, J Virol Methods, 151:172-180, 2008). The purpose of a vaccine carrier platform is to provide the structural and immunologic framework to enhance the immune responses to heterologous B and/or T cell epitopes inserted therein. The more focused the immune response is on the heterologous epitopes and the less on the endogenous B cell epitopes of the carrier, the better. Carrier-specific antibodies may impede the immunogenicity of the heterologous epitopes and may attenuate the response in individuals who receive vaccinations at different times for different pathogens based on the same carrier (Renjifo et al., J Immunol, 161:702-706, 1998).

Thus what the art needs are vaccine carrier platforms with diminished carrier-specific antigenicity. In particular, hepadnavirus core antigens engineered to possess fewer endogenous B cell epitopes are desirable.

SUMMARY

The present disclosure generally relates to rodent hepadnavirus core antigens in which one or more endogenous B cell epitopes have been effectively removed. More specifically, the present disclosure relates to rodent hepadnavirus cores modified to diminish the antibody response to the core so as to enhance the antibody response to heterologous polypeptides included therein.

The present disclosure provides antigenic composition comprising a hybrid rodent hepadnavirus core antigen, wherein the hybrid core antigen is a fusion protein comprising a heterologous antigen and a rodent hepadnavirus core antigen with reduced antigenicity, and wherein said fusion protein is capable of assembling as a hybrid virus-like particle (VLP). In some embodiments, the rodent hepadnavirus is a woodchuck hepadnavirus core antigen, while in other embodiments the rodent hepadnavirus core antigen is a ground squirrel or arctic ground squirrel core antigen. In some embodiments, the woodchuck hepadnavirus core antigen with reduced antigenicity comprises SEQ ID NO:12 or SEQ ID NO:13, but does not comprise SEQ ID NO:11 or SEQ ID NO:1. In some embodiments, the woodchuck hepadnavirus core antigen with reduced antigenicity comprises one of the amino acid sequences selected from the group consisting of SEQ ID NO:2, SEQ ID NO:3, SEQ ID NO:4, SEQ ID NO:5, SEQ ID NO:6 and SEQ ID NO:7. In some embodiments, the woodchuck hepadnavirus core antigen with reduced antigenicity comprises one, two, three, four or five modifications of the group consisting of:

Δ2=WHcAg/L21A, D26A, L27A, N28A, A29V, V31A substitutions;
Δ3=WHcAg/N136P, A137P substitutions;
Δ4=WHcAg/C61S substitution;
Δ5=WHcAg/replacement of residues 62-85, 65-88 or 64-87 with a heterologous antigen;
Δ6=WHcAg/R150A, R151A, R152A, R156A, R159A, R162A, R163A, R164A, R169A, R170A, R171A, R177A, R178A, R179A, R180A substitutions; and
Δ7=WHcAg/N75A, I76A, T77A, S78A, E79A, Q80A, V81A, R82A, T83A substitutions;
wherein the modifications are numbered according to SEQ ID NO:1. In some embodiments, the heterologous antigen is from 4 to 50 amino acids in length. In some embodiments, the heterologous antigen is inserted at a position within the core antigen selected from the group consisting of N-terminal, 44, 71, 72, 73, 74, 75, 76, 77, 78, 81, 82, 83, 84, 85, 92, 149 and C-terminal, as numbered according to SEQ ID NO:1. In some embodiments, the heterologous antigen is inserted at a position within the core antigen selected from the group consisting of 74, 76, 78, 81 and 82. In some embodiments, the hybrid VLP binds to a heterologous antigen-specific antibody. In some embodiments, the hybrid VLP competes with a native or recombinant form of the heterologous antigen for binding to a heterologous antigen-specific antibody. In some embodiments, the hybrid VLP elicits a high titer, antibody response against the heterologous antigen. In some embodiments, the hybrid VLP elicits a measurable neutralizing antibody response against a pathogen comprising the heterologous antigen. In some embodiments, the hybrid VLP elicits an intermediate to high titer neutralizing antibody response against a pathogen comprising the heterologous antigen. In some embodiments, the hybrid virus-like particle (VLP) comprises a combination of two, three, four, or five different hybrid VLPs. The present disclosure also provides a vaccine comprising an adjuvant and any of the antigenic compositions described above The present disclosure further provides methods for eliciting an immune response in an animal in need thereof, comprising administering to the animal an effective amount of the antigenic composition. In some embodiments, the animal is a mammal. In brief, the antigenic composition comprises a hybrid woodchuck hepadnavirus core antigen, wherein the hybrid core antigen is a fusion protein comprising a heterologous antigen and a woodchuck hepadnavirus core antigen, and wherein the fusion protein is capable of assembling as a hybrid virus-like particle (VLP). Various hybrid core antigens for use with the methods are described in detail in the preceding paragraph of the summary. In some embodiments, the immune response comprises a heterologous antigen-reactive antibody response. In some embodiments, when the heterologous antigen is a microbial polypeptide, the present disclosure provides a method for reducing infection with a microbe or preventing disease caused by the microbe in a mammal in need thereof, comprising administering to the mammal an effective amount of the antigenic composition (e.g., vaccine) of the present disclosure according to a suitable vaccine regimen comprising an initial immunization and one or more subsequent immunizations. In some embodiments, the mammal is a human. In some embodiments, the human is a baby (for early childhood immunization methods). In some embodiments the human is a pregnant female (for maternal immunization methods). In some embodiments, the present disclosure provides a method for protecting a baby against microbial infection or microbial disease, comprising administering an effective amount of the antigenic composition to a pregnant female carrying a baby so as to increase microbe-specific antibodies of the pregnant female, wherein a portion of the microbe-specific antibodies are transferred via the female's placenta to the baby during gestation, and/or transferred via breast milk to the baby after birth, thereby protecting the baby against microbial infection or microbial disease. In some embodiments, the baby is a fetus (e.g., unborn baby), a neonate (e.g., newborn less than one month old), or an infant (e.g., one to 12 months old). In some embodiments, the microbe-specific antibodies are detectable in serum of the baby at or following birth. In some embodiments, the microbe-specific antibodies comprise IgG antibodies. In some embodiments, the IgG antibodies are microbe-neutralizing antibodies. In some embodiments, protecting the baby against microbial infection comprises reducing microbe titers in nasal secretions or blood of the baby after exposure to the microbe as compared to that of a microbe-infected baby. In some aspects, the subsequent immunization is in one boost. In other aspects, the subsequent immunization is in two boosts.

In additional embodiments, the present disclosure provides a method for screening anti-heterologous antigen (hAg) antibodies comprising: a) measuring binding of an antibody or fragment thereof to a hybrid woodchuck hepadnavirus core antigen, wherein the hybrid core antigen is a fusion protein comprising a hAg and a woodchuck hepadnavirus core antigen, and wherein said fusion protein assembles as a hybrid virus-like particle (VLP); and b) measuring binding of the antibody or fragment thereof to a woodchuck hepadnavirus VLP devoid of the hAg; and c) determining that the antibody or fragment thereof is specific for the hAg when the antibody or fragment thereof binds to the hybrid VLP but not the woodchuck hepadnavirus VLP devoid of the hAg. Various hybrid core antigens for use with the methods are described in detail in the preceding paragraphs of the summary. Additionally the present disclosure provides polynucleotides encoding a hybrid rodent hepadnavirus core antigen, wherein the hybrid core antigen is a fusion protein comprising a heterologous antigen and a rodent hepadnavirus core antigen. In some embodiments, the rodent hepadnavirus is a woodchuck hepadnavirus core antigen, while in other embodiments the rodent hepadnavirus core antigen is a ground squirrel or arctic ground squirrel core antigen. In some embodiments, the heterologous antigen is inserted at a position within the woodchuck hepadnavirus core antigen selected from the group consisting of N-terminal, 44, 71, 72, 73, 74, 75, 76, 77, 78, 81, 82, 83, 84, 85, 92, 149 and C-terminal as numbered according to SEQ ID NO:1. In some embodiments, the amino acid sequence of the hybrid core antigen is one of SEQ ID NOS:2-7 or is at least 95% identical to one of SEQ ID NOS:2-7, but does not comprise SEQ ID NO:1 or SEQ ID NO:11. Various hybrid core antigens are described in detail in the preceding paragraphs of the summary. Also provides are expression constructs comprising the polynucleotide in operable combination with a promoter. The disclosure further provides expression vectors comprising the expression construct, and host cells comprising the expression vector.

BRIEF DESCRIPTION OF THE DRAWINGS

FIG. 1A provides an alignment of amino acid sequences of core antigens from woodchuck (WHcAg), ground squirrel (GScAg), arctic ground squirrel (AGScAg) and human (HBcAg) hepadnaviruses. Δ2-Δ7 show the amino acid changes relative to WHcAg. Dots under the sequence indicate no change from the WHcAg amino acid sequence. Underlined amino acids denote differences relative to WHcAg within the boxed regions. The amino acid sequences of the core antigens are set forth as follows: WHcAg as SEQ ID NO:1; delta2WHcAg as SEQ ID NO:2; delta3WHcAg as SEQ ID NO:3; delta4WHcAg as SEQ ID NO:4; delta5WHcAg as SEQ ID NO:5; delta6WHcAg as SEQ ID NO:6; delta7WHcAg as SEQ ID NO:7; GScAg as SEQ ID NO:8, AGScAg as SEQ ID NO:9; and HBcAg as SEQ ID NO:10.

FIG. 1C provides a flow chart for the screening of hybrid virus-like particles (VLPs) for use in antigenic, immunogenic and vaccine formulations.

DESCRIPTION

The present disclosure generally relates to rodent hepadnavirus core antigens in which one or more endogenous B cell epitopes have been effectively removed. More specifically, the present disclosure relates to rodent hepadnavirus cores modified to diminish the antibody response to the core so as to enhance the antibody response to heterologous polypeptides included therein.

Rodent Hepadnavirus Core Antigens

Figure 1B:
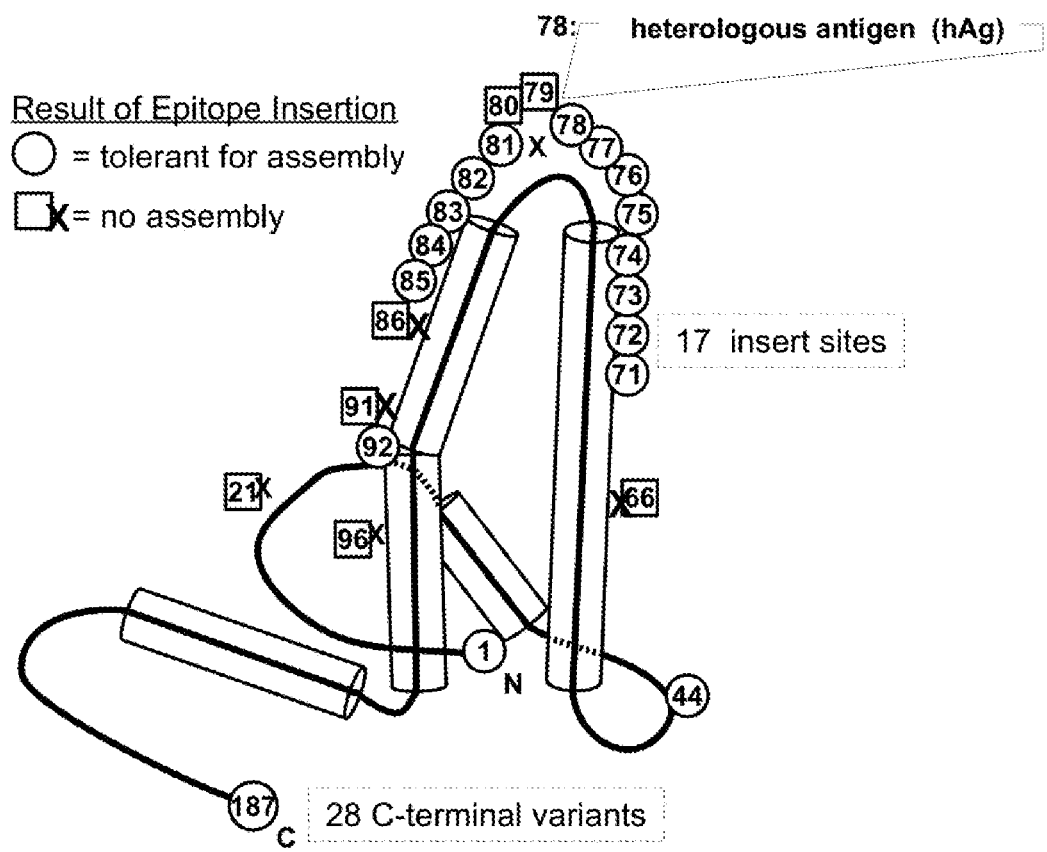
FIG. 1B provides a schematic of the woodchuck hepadnavirus core antigen (WHcAg) structure illustrating positional tolerance for epitope insertions. Circles indicate insert positions that are tolerant for particle assembly including positions: 1 (N-terminus), 44, 71, 72, 73, 74, 75, 76, 77, 78, 81, 82, 83, 84, 85, 92, and 187 (C-terminus). The C-terminus of WHcAg truncated at residue 149 (e.g., devoid of residues 150-188) is also tolerant for particle assembly. In contrast, squares indicate insert positions that are intolerant for particle assembly including positions: 21, 66, 79, 80, 86 and 91. Position numbering is based on the full length WHcAg amino acid sequence set forth as SEQ ID NO:1. The WHcAg truncated at position 149 is set forth as SEQ ID NO:11.
Figure 2:
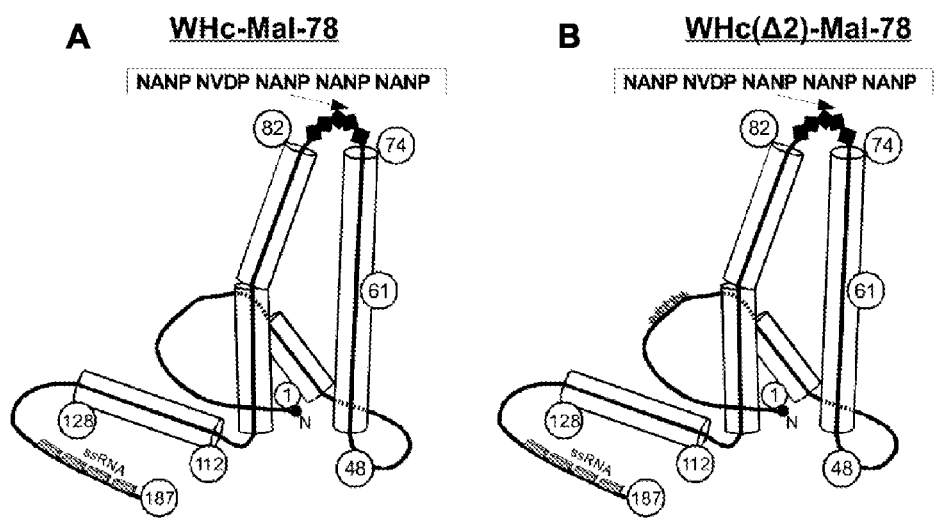
FIGS. 2A and 2B provide schematics of hybrid WHcAg-Malaria virus-like particles (VLPs). The VLP of FIG. 2A is based on a full-length WHcAg, while the VLP of FIG. 2B is based on a modified, full length WHcAg (Δ2WHcAg) in which the B cell epitope within residues 21-31 of the carrier has been removed. The amino acid sequence of the malaria epitope, NANP NVDP NANP NANP NANP is set forth as SEQ ID NO:14.

Exemplary rodent hepadnavirus core antigens of the present disclosure include woodchuck (WHcAg), ground squirrel (GScAg), arctic ground squirrel (AGScAg) hepadnavirus core antigens. The amino acid sequences of reference rodent hepadnavirus core antigens are shown in the alignment of FIG. 1A. Rodent hepadnavirus core antigens have been chosen as carriers in part because they are multimeric, self-assembling, virus-like particles (VLP). The basic subunit of the core particle is a 21 kDa polypeptide monomer that spontaneously assembles into a 240 subunit particulate structure of about 34 nm in diameter. The tertiary and quaternary structures of hepadnavirus core particles have been elucidated (Conway et al., Nature, 386:91-94, 1997) and is shown schematically in FIG. 1B. The immunodominant B cell epitope on WHcAg is localized around amino acids 76-82 (Schodel et al., J Exp Med, 180:1037-1046, 1994) forming a loop connecting adjacent alpha-helices. This observation is consistent with the finding that a heterologous antigen inserted within the 76-82 loop region of HBcAg was significantly more antigenic and immunogenic than the antigen inserted at the N- or C-termini and, importantly, more immunogenic than the antigen in the context of its native protein (Schodel et al., J Virol, 66:106-114, 1992).

Although several HBcAg-specific B cell epitopes have been identified, very little has been published regarding WHcAg-specific B cell epitopes, with the exception of a single study that mapped a WHcAg-specific B cell epitope to the extreme N-terminus of denatured WHcAg (Zhang et al., J Virol Methods, 135:17-25, 2006). Additionally, all the work on HBcAg has been performed on native HBcAg, as opposed to hybrid-core particles (Belnap et al., Proc Natl Acad Sci USA, 100:10884-10889, 2003; Conway et al., J Mol Biol, 279:1111-1121, 1998; Conway et al., J Virol, 77:6466-6473, 2003; and Harris et al., J Mol Biol, 355:562-576, 2006).

One of the first steps taken during development of the present disclosure was to generate a panel of eight monoclonal antibodies (MAbs) specific for the WHcAg. Table I lists the MAb names and characteristics. Table II is a summary of the carrier binding specificity of the anti-WHcAg MAb panel. As shown in Table II, most WHcAg-specific MAbs show cross-reactivity with other rodent hepadnavirus core antigens but none show significant recognition of a duck hepadnavirus core antigen. Additionally, most of the MAbs did not recognize a (1-78)HBcAg/(78-187)WHcAg hybrid particle, but did recognize a (1-78)WHcAg/(79-183HBcAg hybrid particle suggesting a bias for the N-terminal half of the WHcAg.

TABLE I

Anti-WHcAg Monoclonal Antibodies

| Mab Name | Specificity |
|---|---|
| 6D10 | WHcAg residues 21-31 |
| 4H11 | Unknown WHcAg specificity, weakly cross reactive with HBcAg |
| 1F10 | WHcAg residues 21-31 plus additional residues within WHcAg 1-78 |
| 1A12 | WHcAg residues 61-74 |
| 13B5 | Native WHcAg particles |
| 1A9 | Unknown WHcAg specificity, weakly cross reactive with HBcAg |
| 15F1 | Unknown WHcAg specificity, strongly cross reactive with HBcAg |
| 5A10 | WHcAg residues 21-31 plus additional residues within WHcAg |

TABLE II

Anti-WHcAg Monoclonal Antibody Recognition of Various Hepadnavirus Cores

| Core Particles | Monoclonal Antibodies | | | | | | | Polyclonal |
|---|---|---|---|---|---|---|---|---|
| | 6D10 | 4H11 | 1F10 | 1A12 | 13B5 | 1A9 | 15F1 | α-WHc |
| Native | | | | | | | | |
| WHcAg | 0.7 | 1.7 | 1.5 | 0.9 | 1.1 | 1.1 | 0.9 | 1.3 |
| HBcAg | 0 | 0.6 | 0 | 0 | 0 | 0.3 | 1.2 | 0.4 |
| GScAg | 2.0 | 1.4 | 0.8 | 0.4 | 0 | 0.7 | 2.0 | 0.2 |
| AGScAg | 0.8 | 1.2 | 0.2 | 0.1 | 0 | 0.4 | 1.3 | 0.1 |
| DHcAg | 0 | 0.2 | 0 | 0 | 0 | 0 | 0 | 0 |
| Hybrid | | | | | | | | |
| HBcAg/WHcAg | 0 | 0.9 | 0 | 0 | 0 | 0.3 | 0.3 | 0.1 |
| WHcAg/HBcAg | 1.4 | 1.7 | 1.6 | 0.92 | 0 | 1.0 | 1.4 | 0.1 |

Binding is shown as OD units, with values ≤0.3 OD units indicative of a lack of recognition (e.g., little to no binding).

Next, a series of recombinant WHcAg particles containing various mutations were produced, as listed in Table III. The WHcAg particles were designed to include either a heterologous B cell epitope within the WHcAg immunodominant loop extending from residues 76-82 of wild type WHcAg (Δ1 mutation), or alter endogenous WHcAg-specific B cell epitopes in order to reduce WHcAg-specific antigenicity and/or immunogenicity without negatively affecting the antigenicity and/or immunogenicity of heterologous B cell epitopes inserted within the WHcAg. The mutations designed to decrease WHcAg-specific antigenicity and/or immunogenicity are designated as Δ2-Δ7 mutations or modifications. These new varieties of modified WHcAg carrier platforms provide an advantageous system for presentation of heterologous antigens (hAg).

In some embodiments, the woodchuck hepadnavirus core antigen with reduced antigenicity comprises one, two, three, four or five modifications of the group consisting of the Δ2-Δ7 modifications. Exemplary combinations of modifications include: Δ2 and one or more of Δ3, Δ4, Δ5, Δ6.x and Δ7.x; Δ3 and one or more of Δ2, Δ4, Δ5, Δ6.x and Δ7.x; Δ4 and one or more of Δ2, Δ3, Δ5, Δ6.x and Δ7.x; Δ5 and one or more of Δ2, Δ3, Δ4, Δ6.x and Δ7.x; Δ6 and one or more of Δ2, Δ3, Δ4, Δ5.x and Δ7.x; and Δ7 and one or more of Δ2, Δ3, Δ4, Δ5.x and Δ6.x.

In some embodiments, the present disclosure provides a woodchuck hepadnavirus core antigen with reduced antigenicity, which comprises SEQ ID NO:12, SEQ ID NO:13, or a variant thereof that is at least 90% (e.g., 90%, 91%, 92%, 93%, 94%, 95%, 96%, 97%, 98%, or 99% identical) to SEQ ID NO:12 or SEQ ID NO:13, but does not comprise SEQ ID NO:11 or SEQ ID NO:1. In some embodiments, the woodchuck hepadnavirus core antigen with reduced antigenicity comprises one of the amino acid sequences selected from the group consisting of SEQ ID NO:2, SEQ ID NO:3, SEQ ID NO:4, SEQ ID NO:5, SEQ ID NO:6 and SEQ ID NO:7.

TABLE III

WHcAg Mutations Affecting Antigenicity and/or Immunogenicity

| Designation | Description |
|---|---|
| Δ1 | WHcAg/insertion of a heterologous antigen within the immunodominant loop |
| Δ2 | WHcAg/L21A, D26A, L27A, N28A, A29V, V31A substitutions |
| Δ3 | WHcAg/N136P, A137P substitutions |
| Δ4 | WHcAg/C61S substitution |
| Δ5 | WHcAg/replacement of residues 62-85, 65-88 or 64-87 with a heterologous antigen |
| Δ6 | WHcAg/R150A, R151A, R152A, R156A, R159A, R162A, R163A, R164A, R169A, R170A, R171A, R177A, R178A, R179A, R180A substitutions |
| Δ6.1 | WHcAg/R150A, R151A, R152A, R156A, R159A, R162A, R163A, R164A, R169A, R170A, R171A substitutions |
| Δ7 | WHcAg/N75A, I76A, T77A, S78A, E79A, Q80A, V81A, R82A, T83A substitutions |
| Δ7.1 | WHcAg/N75A, I76S, T77S, S78E, E79L, Q80E, V81L, R82E, T83L substitutions |

Combinatorial Technology

A problem inherent to the insertion of heterologous epitope sequences into VLP genes is that such manipulation can abolish self-assembly. This assembly problem is so severe that several groups working with the HBcAg or with other VLP technologies (e.g., the L1 protein of the human papillomavirus and Qβ phage) have opted to chemically link the foreign epitopes to the VLPs rather than inserting the epitopes into the particles by recombinant methods. The need to chemically conjugate heterologous antigens has been circumvented by development of combinatorial technology (Billaud et al., J Virol, 79:13656-13666, 2005). This was achieved by determining 17 different insertion sites and 28 modifications of the WHcAg C-terminus that together favor assembly of chimeric particles, as well as the identification of a number of additional improvements (see, e.g., U.S. Pat. Nos. 7,144,712; 7,320,795; and 7,883,843). ELISA-based screening systems have been developed that measure expression levels, VLP assembly, and insert antigenicity using crude bacterial lysates, avoiding the need to employ labor-intensive purification steps for hybrid VLPs that do not express and/or assemble well.

Heterologous Antigens

A heterologous antigen (hAg) of the present disclosure is a polypeptide that is different from a rodent hepadnavirus core antigen. In particular, when used to refer to a portion of a fusion protein or a hybrid core antigen comprising a rodent hepadnavirus core antigen and a heterologous antigen, the term heterologous antigen refers to the portion, which is not derived from or does not otherwise correspond to the rodent hepadnavirus core antigen. In some embodiments, the heterologous antigen is a polypeptide of from 4 to 60 amino acids in length. In some embodiments, the heterologous antigen is from 5 to 55 amino acids in length, preferably 10 to 50 amino acids in length, preferably 15 to 45 amino acids in length, or preferably 20 to 40 amino acids in length. In some embodiments, the length of the heterologous antigen is within any range having a lower limit of 4, 5, 6, 7, 8, 9, 10, 11, 12, 13, 14, 15, 16, 17, 18, 19 or 20 amino acids and an independently selected upper limit of 60, 55, 50, 45, 40, 35, 30, 25 or 20 amino acids in length, provided that the lower limit is less than the upper limit.

In some embodiments, the heterologous antigen comprises one B cell epitope, while in others it comprises two, three, four or five B cell epitopes, or even a larger plurality of B cell epitopes. In some preferred embodiments, the heterologous antigen further comprises one T cell epitope, or it comprises two, three, four or five T cell epitopes, or even a larger plurality of T cell epitopes. In some embodiments, the T cell epitope is a helper T (Th) cell epitope (MHC class II-restricted epitope). In some embodiments, the T cell epitope is a cytotoxic T cell (CTL) epitope (MHC class I-restricted epitope). Determination as to whether a given heterologous antigen of a hybrid core antigen comprises a B cell epitope can be made by analyzing heterologous antigen-specific antibody-binding of serum of a subject immunized with the hybrid core antigen (or polynucleotide encoding the hybrid core antigen). Determination as to whether a given heterologous antigen of a hybrid core antigen comprises a Th cell epitope can be made by analyzing heterologous antigen-induced proliferation or cytokine secretion by peripheral blood lymphocytes (PBL) of a subject immunized with the hybrid core antigen (or polynucleotide encoding the hybrid core antigen). Determination as to whether a given heterologous antigen of a hybrid core antigen comprises a CTL cell epitope can be made by analyzing heterologous antigen-specific lysis of a target cell that expresses the heterologous antigen by CTL expanded from PBL of a subject immunized with a polynucleotide encoding the hybrid core antigen. Other methods of determining whether a heterologous antigen or fragment thereof comprises B, Th and/or CTL epitopes are known in the art.

In some embodiments, the heterologous antigen is a microbial polypeptide. Microbial polypeptides of the present disclosure include viral, bacterial, fungal and parasitic (protozoa and nematodes) polypeptides. In other embodiments, the heterologous antigen is an allergen. In still further embodiments, the heterologous antigen is a cancer antigen. In some embodiments, the heterologous antigen comprises a fragment of a surface protein. In other embodiments, the heterologous antigen comprises a fragment of a secreted protein. In other embodiments, the heterologous antigen comprises a fragment of a cytosolic protein. In still further embodiments, the heterologous antigen is itself a fusion protein comprising fragments of two, three, four or five different polypeptides.

Heterologous antigens that comprise microbial polypeptides, preferably include polypeptides of microbes that cause disease in humans or other mammals. Microbes causing disease in humans include but are not limited to adenovirus (types 4 and 7), anthrax bacterium (*Bacillus anthracis*), tuberculosis bacterium (*Mycobacterium tyberculosis*), diphtheria bacterium (*Corynebacterium diphtheria*), tetanus bacterium (*Clostridium tetani*), pertussis bacterium (*Bordetella pertussis*), haemophilus bacterium (e.g., *Haemophilus influenza*), human hepatitis virus (types A, B and C), human papillomavirus virus (types 6, 11, 16 and 18), influenza virus (types A and B), Japanese encephalitis virus, measles virus, mumps virus, rubella virus, poliovirus, rabies virus, rotavirus, variola virus (small pox virus), typhoid bacterium (*Salmonella enterica*), varicella zoster virus (chicken pox and shingles virus), and yellow fever virus. Additional microbes causing disease in humans include but are not limited to *Trypanosoma brucei* (African sleeping sickness or African trypanosomiasis parasite), human immunodeficiency virus-1 (HIV-1 or acquired immunodeficiency syndrome virus) *Trypanosoma cruzi* (Chagas disease or American trypanosomiasis parasite), *Chlamydia trachomatis* (*chlamydia* bacterium), *Vibrio cholera* (cholera bacterium), dengue fever virus, ebolavirus (Ebola hemorrhagic fever virus), hantavirus (Sin Nombre virus), herpes simplex virus (types 1 and 2), *Leishmania* sp. parasite, *Mycobacterium lepromatosis* (leprosy bacterium), *Borrelia burgdorferi* (Lyme disease bacterium), malarial parasites (*Plasmodium falciparum*, *Plasmodium vivax*, *Plasmodium ovale*, *Plasmodium malariae*, and *Plasmodium knowlesi*), *Neisseria meningitidis* (meningococcal disease bacterium), *Neisseria gonorrhoeae* (gonorrhoeae bacterium), norovirus, *Yersinia pestis* (plague bacterium), respiratory syncytial virus, severe acute respiratory syndrome virus (SARS coronavirus), *Treponema pallidum* (syphilis bacterium), and West Nile virus.

Development of Fusion Proteins and Hybrid Particles

As depicted in FIG. 1B, a number of insertion sites inside the loop region (positions 76-82), as well as outside the loop region are tolerated by WHcAg. The hybrid VLPs of the present disclosure can be grouped into several categories as listed in Table IV.

TABLE IV

Categories of Hybrid, WHcAg-hAg VLP Mutants

| Category | Description |
|---|---|
| standard | heterologous polypeptide inserted at position 78 within the immunodominant loop |
| epitope-modified | alterations affecting the heterologous polypeptide |
| carrier-modified | alterations affecting the WHcAg carrier |
| linker-modified | addition or deletion of heterologous polypeptide linkers |
| varied position | insertion of the heterologous polypeptide at a position tolerant of assembly other than position 78 of the WHcAg carrier |
| replacement | replacement of WHcAg carrier residues with a heterologous polypeptide |

Antigenic and Immunogenic Characterization of Hybrid, WHcAg-hAg VLPs

A. Antigenicity

Prior to immunogenicity testing, hybrid WHcAg-hAg VLPs are characterized for expression, particle assembly, and ability to bind a hAg-specific antibody. The same capture ELISA system used to detect hybrid VLPs in bacterial lysates may be used for purified particles. In brief, expression, particle assembly, and antibody binding are assayed by ELISA. SDS-PAGE and Western blotting are used to assess the size and antigenicity of hybrid VLPs.

B. Immunogenicity

The immune response to hybrid VLPs is assessed. In addition to anti-insert, anti-hAg-protein and anti-WHcAg antibody endpoint titers, antibody specificity, isotype distribution, antibody persistence and antibody avidity are monitored. Immune sera are compared to the activity of a reference antibody by ELISA and neutralization assays. Immune responses are tested in vivo in various mammalian species (e.g., rodents such as rats and mice, nonhuman primates, humans, etc.).

Compositions

The compositions of the present disclosure comprise a hybrid woodchuck hepadnavirus core antigen or a polynucleotide encoding the hybrid core antigen, wherein the hybrid core antigen is a fusion protein comprising a heterologous polypeptide and a woodchuck hepadnavirus core antigen, wherein the fusion protein is capable of assembling as a hybrid virus-like particle (VLP). In some embodiments, the heterologous polypeptide comprises at least one B cell epitope (e.g., capable of being bound by an antibody). In preferred embodiments, the composition is an antigenic composition. In some embodiments, the composition further comprises a pharmaceutically acceptable carrier. The term "carrier" refers to a vehicle within which the hybrid core antigen or polynucleotide encoding the antigen is administered to a mammalian subject. The term carrier encompasses diluents, excipients, adjuvants and combinations thereof. Pharmaceutically acceptable carriers are well known in the art (see, e.g., Remington's Pharmaceutical Sciences by Martin, 1975).

Exemplary "diluents" include sterile liquids such as sterile water, saline solutions, and buffers (e.g., phosphate, tris, borate, succinate, histidine, etc.). Exemplary "excipients" are inert substances include but are not limited to polymers (e.g., polyethylene glycol), carbohydrates (e.g., starch, glucose, lactose, sucrose, cellulose, etc.), and alcohols (e.g., glycerol, sorbitol, xylitol, etc.).

Adjuvants are broadly separated into two classes based upon their primary mechanism of action: vaccine delivery systems (e.g., emulsions, microparticles, iscoms, liposomes, etc.) that target associated antigens to antigen presenting cells (APC); and immunostimulatory adjuvants (e.g., LPS, MLP, CpG, etc.) that directly activate innate immune responses. The WHcAg platform provides a delivery system that targets antigen specific B cells and other primary APC, as well as efficient T cell help for antigen-specific B cells. Additionally, the core platform functions as an immunostimulatory adjuvant by directly activating antigen-specific B cells by virtue of cross-linking membrane immunoglobulin (mIg) receptors for induction of B7.1 and B7.2 costimulatory molecule expression on naive resting B cells (Milich et al., Proc Natl Acad Sci USA, 94:14648-14653, 1997).

A. Traditional and Molecular Adjuvants

Although adjuvants are not required when using the WHcAg delivery system, some embodiments of the present disclosure employ traditional and/or molecular adjuvants. Specifically, immunization in saline effectively elicits anti-insert antibody production. However, formulation in non-inflammatory agents such as IFA (mineral oil), Montanide ISA 720 (squalene), and aluminum phosphate (AlPO4), enhance immunogenicity. Additionally, administration of WHcAg results in the production of all four IgG isotypes, regardless of which if any adjuvant is employed. Inclusion of a CpG motif also enhances the primary response. Moreover, use of an inflammatory adjuvant such as the Ribi formulation is not more beneficial than is the use of non-inflammatory adjuvants, indicating that the benefits of the adjuvants result from a depot effect rather than from non-specific inflammation. Thus, the core platform is used with no adjuvant or with non-inflammatory adjuvants depending upon the application and the quantity of antibody desired. In some embodiments of the present disclosure, IFA is used in murine studies, whereas alum or squalene is used in human studies. In instances where it is desirable to deliver hybrid WHcAg particles in a single dose in saline, a molecular adjuvant is employed. A number of molecular adjuvants are employed to bridge the gap between innate and adaptive immunity by providing a co-stimulus to target B cells or other APCs.

B. Other Molecular Adjuvants

Genes encoding the murine CD40L (both 655 and 470 nucleic acid versions) have been used successfully to express these ligands at the C-terminus of WHcAg (See, WO 2005/011571). Moreover, immunization of mice with hybrid WHcAg-CD40L particles results in the production of higher anti-core antibody titers than does the immunization of mice with WHcAg particles. However, lower than desirable yields of purified particles have been obtained. Therefore, mosaic particles containing less than 100% CD40L-fused polypeptides are produced to overcome this problem. The other molecular adjuvants inserted within the WHcAg, including the C3d fragment, BAFF and LAG-3, have a tendency to become internalized when inserted at the C-terminus. Therefore tandem repeats of molecular adjuvants are used to resist internalization. Alternatively, various mutations within the so-called hinge region of WHcAg, between the assembly domain and the DNA/RNA-binding region of the core particle are made to prevent internalization of C-terminal sequences. However, internalization represents a problem for those molecular adjuvants such as CD40L, C3d, BAFF and LAG-3, which function at the APC/B cell membrane. In contrast, internalization of molecular adjuvants such as CpG DN is not an issue as these types of adjuvants function at the level of cytosolic receptors.

Another type of molecular adjuvant or immune enhancer is the inclusion within hybrid core particles of a CD4+ T cell epitope, preferably a "universal" CD4+ T cell epitope that is recognized by a large proportion of CD4+ T cells (such as by more than 50%, preferably more than 60%, more preferably more than 70%, most preferably greater than 80%), of CD4+ T cells. In one embodiment, universal CD4+ T cell epitopes bind to a variety of human MHC class II molecules and are able to stimulate T helper cells. In another embodiment, universal CD4+ T cell epitopes are preferably derived from antigens to which the human population is frequently exposed either by natural infection or vaccination (Falugi et al., Eur J Immunol, 31:3816-3824, 2001). A number of such universal CD4+ T cell epitopes have been described including, but not limited to: Tetanus Toxin (TT) residues 632-651; TT residues 950-969; TT residues 947-967, TT residues 830-843, TT residues 1084-1099, TT residues 1174-1189 (Demotz et al., Eur J Immunol, 23:425-432, 1993); Diphtheria Toxin (DT) residues 271-290; DT residues 321-340; DT residues 331-350; DT residues 411-430; DT residues 351-370; DT residues 431-450 (Diethelm-Okita et al., J Infect Dis, 1818:1001-1009, 2000); *Plasmodium falciparum* circumsporozoite (CSP) residues 321-345 and CSP residues 378-395 (Hammer et al., Cell, 74:197-203, 1993); Hepatitis B antigen (HBsAg) residues 19-33 (Greenstein et al., J Immunol, 148:3970-3977, 1992); Influenza hemagglutinin residues 307-319; Influenza matrix residues 17-31 (Alexander et al., J Immunol, 164:1625-1633, 2000); and measles virus fusion protein (MVF) residues 288-302 (Dakappagari et al., J Immunol, 170:4242-4253, 2003).

Methods of Inducing an Immune Response

The present disclosure provides methods for eliciting an immune response in an animal in need thereof, comprising administering to the animal an effective amount of an antigenic composition comprising a hybrid woodchuck hepadnavirus core antigen, wherein the hybrid core antigen is a fusion protein comprising a heterologous antigen and a woodchuck hepadnavirus core antigen with reduced antigenicity, and wherein said fusion protein assembles as a hybrid virus-like particle (VLP). Also provided by the present disclosure are methods for eliciting an immune response in an animal in need thereof, comprising administering to the animal an effective amount of an antigenic composition comprising a polynucleotide encoding a hybrid woodchuck hepadnavirus core antigen, wherein the hybrid core antigen is a fusion protein comprising a heterologous antigen and a woodchuck hepadnavirus core antigen with reduced antigenicity, and wherein said fusion protein assembles as a hybrid virus-like particle (VLP). Unless otherwise indicated, the antigenic composition is an immunogenic composition.

The immune response raised by the methods of the present disclosure generally includes an antibody response, preferably a neutralizing antibody response, preferably a protective antibody response. Methods for assessing antibody responses after administration of an antigenic composition (immunization or vaccination) are well known in the art. In some embodiments, the immune response comprises a T cell-mediated response (e.g., heterologous antigen-specific response such as a proliferative response, a cytokine response, etc.). In preferred embodiments, the immune response comprises both a B cell and a T cell response. Antigenic compositions can be administered in a number of suitable ways, such as intramuscular injection, subcutaneous injection, and intradermal administration. Additional modes of administration include but are not limited to intranasal administration, and oral administration.

Antigenic compositions may be used to treat both children and adults, including pregnant women. Thus a subject may be less than 1 year old, 1-5 years old, 5-15 years old, 15-55 years old, or at least 55 years old. Preferred subjects for receiving the vaccines are the elderly (e.g., >55 years old, >60 years old, preferably >65 years old), and the young (e.g., <6 years old, 1-5 years old, preferably less than 1 year old).

Administration can involve a single dose or a multiple dose schedule. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, etc. Administration of more than one dose (typically two doses) is particularly useful in immunologically naive subjects or subjects of a hyporesponsive population (e.g., diabetics, subjects with chronic kidney disease, etc.). Multiple doses will typically be administered at least 1 week apart (e.g., about 2 weeks, about 3 weeks, about 4 weeks, about 6 weeks, about 8 weeks, about 10 weeks, about 12 weeks, about 16 weeks, and the like.). Preferably multiple doses are administered from one, two, three, four or five months apart. Antigenic compositions of the present disclosure may be administered to patients at substantially the same time as (e.g., during the same medical consultation or visit to a healthcare professional) other vaccines.

In general, the amount of protein in each dose of the antigenic composition is selected as an amount effective to induce an immune response in the subject, without causing significant, adverse side effects in the subject. Preferably the immune response elicited is a neutralizing antibody, preferably a protective antibody response. Protective in this context does not necessarily mean the subject is completely protected against infection, rather it means that the subject is protected from developing symptoms of disease, especially severe disease associated with the pathogen corresponding to the heterologous antigen.

The amount of hybrid core antigen (e.g., VLP) can vary depending upon which antigenic composition is employed.

Generally, it is expected that each human dose will comprise 1-1500 µg of protein (e.g., hybrid core antigen), such as from about 1 µg to about 1000 µg, for example, from about 1 µg to about 500 µg, or from about 1 µg to about 100 µg. In some embodiments, the amount of the protein is within any range having a lower limit of 10, 20, 30, 40, 50, 60, 70, 80, 90, 100, 110, 120, 130, 140, 150, 160, 170, 180, 190, 200, 210, 220, 230, 240 or 250 µg, and an independently selected upper limit of 1000, 950, 900, 850, 800, 750, 700, 650, 600, 550, 500, 450, 400, 350, 300 or 250 µg, provided that the lower limit is less than the upper limit. Generally a human dose will be in a volume of from 0.1 ml to 1 ml, preferably from 0.25 ml to 0.5 ml. The amount utilized in an immunogenic composition is selected based on the subject population. An optimal amount for a particular composition can be ascertained by standard studies involving observation of antibody titers and other responses (e.g., antigen-induced cytokine secretion) in subjects. Following an initial vaccination, subjects can receive a boost in about 4-12 weeks.

Kits

Also provided by the present disclosure are kits comprising a hybrid woodchuck hepadnavirus core antigen and a woodchuck hepadnavirus core antigen, wherein the hybrid core antigen is a fusion protein comprising a heterologous antigen and a woodchuck hepadnavirus core antigen with reduced antigenicity, and wherein said fusion protein assembles as a hybrid virus-like particle (VLP), and wherein the core antigen lacks the heterologous antigen. In some embodiments, the kits further comprise instructions for measuring heterologous antigen-specific antibodies. In some embodiments, the antibodies are present in serum from a blood sample of a subject immunized with an antigenic composition comprising the hybrid woodchuck hepadnavirus core antigen.

As used herein, the term "instructions" refers to directions for using reagents (e.g., a hybrid core antigen and a core antigen) contained in the kit for measuring antibody titer. In some embodiments, the instructions further comprise the statement of intended use required by the U.S. Food and Drug Administration (FDA) in labeling in vitro diagnostic products. The FDA classifies in vitro diagnostics as medical devices and required that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use, including photographs or engineering drawings, where applicable; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; and 8) Any additional information regarding the in vitro diagnostic product requested that is necessary for the FDA to make a substantial equivalency determination.

Definitions

As used herein, the singular forms "a", "an", and "the" include plural references unless indicated otherwise. For example, "an" excipient includes one or more excipients. The term "plurality" refers to two or more.

The phrase "comprising" as used herein is open-ended, indicating that such embodiments may include additional elements. In contrast, the phrase "consisting of" is closed, indicating that such embodiments do not include additional elements (except for trace impurities). The phrase "consisting essentially of" is partially closed, indicating that such embodiments may further comprise elements that do not materially change the basic characteristics of such embodiments.

The practice of the present disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989); Current Protocols in Molecular Biology (Ausubel et al., eds., 1987); PCR: The Polymerase Chain Reaction, (Mullis et al., eds., 1994); Culture of Animal Cells: A Manual of Basic Technique (Freshney, 1987); Harlow et al., Antibodies: A Laboratory Manual (Harlow et al., 1988); and Current Protocols in Immunology (Coligan et al., eds., 1991).

As used herein, the terms "virus-like particle" and "VLP" refer to a structure that resembles a virus. VLPs of the present disclosure lack a viral genome and are therefore noninfectious. Preferred VLPs of the present disclosure are woodchuck hepadnavirus core antigen (WHcAg) VLPs.

The terms "hybrid" and "chimeric" as used in reference to a hepadnavirus core antigen, refer to a fusion protein of the hepadnavirus core antigen and an unrelated antigen (e.g., bacterial polypeptide, and variants thereof). For instance, in some embodiments, the term "hybrid WHcAg" refers to a fusion protein comprising both a WHcAg component (full length, or partial) and a heterologous antigen or fragment thereof.

The term "heterologous" with respect to a nucleic acid, or a polypeptide, indicates that the component occurs where it is not normally found in nature and/or that it originates from a different source or species.

An "effective amount" or a "sufficient amount" of a substance is that amount necessary to effect beneficial or desired results, including clinical results, and, as such, an "effective amount" depends upon the context in which it is being applied. In the context of administering an immunogenic composition, an effective amount contains sufficient antigen (e.g., hybrid, WHcAg-hAg VLP) to elicit an immune response (preferably a measurable level of hAg pathogen-neutralizing antibodies). An effective amount can be administered in one or more doses.

The term "dose" as used herein in reference to an immunogenic composition refers to a measured portion of the immunogenic composition taken by (administered to or received by) a subject at any one time.

The term "about" as used herein in reference to a value, encompasses from 90% to 110% of that value (e.g., about 200 µg VLP refers to 180 µg to 220 µg VLP).

As used herein the term "immunization" refers to a process that increases an organisms' reaction to antigen and therefore improves its ability to resist or overcome infection.

The term "vaccination" as used herein refers to the introduction of vaccine into a body of an organism.

A "variant" when referring to a polynucleotide or a polypeptide (e.g., a viral polynucleotide or polypeptide) is a polynucleotide or a polypeptide that differs from a reference polynucleotide or polypeptide. Usually, the difference(s) between the variant and the reference constitute a proportionally small number of differences as compared to the reference (e.g., at least 90%, 91%, 92%, 93%, 94%, 95%, 96%, 97%, 98% or 99% identical). In some embodiments, the present disclosure provides hybrid WHcAg-hAg VLPs having at least one addition, insertion or substitution in one or both of the WHcAg or hAg portion of the VLP.

The term "wild type" when used in reference to a polynucleotide or a polypeptide refers to a polynucleotide or a polypeptide that has the characteristics of that polynucleotide or a polypeptide when isolated from a naturally-occurring source. A wild type polynucleotide or a polypeptide is that which is most frequently observed in a population and is thus arbitrarily designated as the "normal" form of the polynucleotide or a polypeptide.

Amino acids may be grouped according to common side-chain properties: hydrophobic (Met, Ala, Val, Leu, Ile); neutral hydrophilic (Cys, Ser, Thr, Asn, Gln); acidic (Asp, Glu); basic (His, Lys, Arg); aromatic (Trp, Tyr, Phe); and orientative (Gly, Pro). Another grouping of amino acids according to side-chain properties is as follows: aliphatic (glycine, alanine, valine, leucine, and isoleucine); aliphatic-hydroxyl (serine and threonine); amide (asparagine and glutamine); aromatic (phenylalanine, tyrosine, and tryptophan); acidic (glutamic acid and aspartic acid); basic (lysine, arginine, and histidine); sulfur (cysteine and methionine); and cyclic (proline). In some embodiments, the amino acid substitution is a conservative substitution involving an exchange of a member of one class for another member of the same class. In other embodiments, the amino acid substitution is a non-conservative substitution involving an exchange of a member of one class for a member of a different class.

The percent identity between the two sequences is a function of the number of identical positions shared by the sequences, taking into account the number of gaps, and the length of each gap, which need to be introduced for optimal alignment of the two sequences. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastn, the default parameters are Gap opening penalty=5 and Gap extension penalty=2. For blastp, the default parameters are Gap opening penalty=11 and Gap extension penalty=1.

A "recombinant" nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques. A "recombinant" protein is one that is encoded by a heterologous (e.g., recombinant) nucleic acid, which has been introduced into a host cell, such as a bacterial or eukaryotic cell. The nucleic acid can be introduced, on an expression vector having signals capable of expressing the protein encoded by the introduced nucleic acid or the nucleic acid can be integrated into the host cell chromosome.

An "antigen" is a compound, composition, or substance that can stimulate the production of antibodies and/or a T cell response in a subject, including compositions that are injected, absorbed or otherwise introduced into a subject. The term "antigen" includes all related antigenic epitopes. The term "epitope" or "antigenic determinant" refers to a site on an antigen to which B and/or T cells respond. The "dominant antigenic epitopes" or "dominant epitope" are those epitopes to which a functionally significant host immune response, e.g., an antibody response or a T-cell response, is made. Thus, with respect to a protective immune response against a pathogen, the dominant antigenic epitopes are those antigenic moieties that when recognized by the host immune system result in protection from disease caused by the pathogen. The term "T-cell epitope" refers to an epitope that when bound to an appropriate MHC molecule is specifically bound by a T cell (via a T cell receptor). A "B-cell epitope" is an epitope that is specifically bound by an antibody (or B cell receptor molecule).

"Adjuvant" refers to a substance which, when added to a composition comprising an antigen, nonspecifically enhances or potentiates an immune response to the antigen in the recipient upon exposure. Common adjuvants include suspensions of minerals (alum, aluminum hydroxide, aluminum phosphate) onto which an antigen is adsorbed; emulsions, including water-in-oil, and oil-in-water (and variants thereof, including double emulsions and reversible emulsions), liposaccharides, lipopolysaccharides, immunostimulatory nucleic acids (such as CpG oligonucleotides), liposomes, Toll-like Receptor agonists (particularly, TLR2, TLR4, TLR7/8 and TLR9 agonists), and various combinations of such components.

An "antibody" or "immunoglobulin" is a plasma protein, made up of four polypeptides that binds specifically to an antigen. An antibody molecule is made up of two heavy chain polypeptides and two light chain polypeptides (or multiples thereof) held together by disulfide bonds. In humans, antibodies are defined into five isotypes or classes: IgG, IgM, IgA, IgD, and IgE. IgG antibodies can be further divided into four subclasses (IgG1, IgG2, IgG3 and IgG4). A "neutralizing" antibody is an antibody that is capable of inhibiting the infectivity of a virus. Accordingly, a neutralizing antibodies specific for a virus are capable of inhibiting or reducing infectivity of the virus.

An "immunogenic composition" is a composition of matter suitable for administration to a human or animal subject (e.g., in an experimental or clinical setting) that is capable of eliciting a specific immune response, e.g., against a pathogen, such as RSV. As such, an immunogenic composition includes one or more antigens (for example, polypeptide antigens) or antigenic epitopes. An immunogenic composition can also include one or more additional components capable of eliciting or enhancing an immune response, such as an excipient, carrier, and/or adjuvant. In certain instances, immunogenic compositions are administered to elicit an immune response that protects the subject against symptoms or conditions induced by a pathogen. In some cases, symptoms or disease caused by a pathogen is prevented (or reduced or ameliorated) by inhibiting replication of the pathogen (e.g., virus) following exposure of the subject to the pathogen. In the context of this disclosure, the term immunogenic composition will be understood to encompass compositions that are intended for administration to a subject or population of subjects for the purpose of eliciting a protective or palliative immune response against a virus (that is, vaccine compositions or vaccines).

An "immune response" is a response of a cell of the immune system, such as a B cell, T cell, or monocyte, to a stimulus, such as a pathogen or antigen (e.g., formulated as an immunogenic composition or vaccine). An immune response can be a B cell response, which results in the production of specific antibodies, such as antigen specific neutralizing antibodies. An immune response can also be a T cell response, such as a CD4+ response or a CD8+ response. B cell and T cell responses are aspects of a "cellular" immune response. An immune response can also be a "humoral" immune response, which is mediated by antibodies. In some cases, the response is specific for a particular antigen (that is, an "antigen-specific response"). If the antigen is derived from a pathogen, the antigen-specific response is a "pathogen-specific response." A "protective immune response" is an immune response that inhibits a detrimental function or activity of a pathogen, reduces infection by a pathogen, or decreases symptoms (including death) that result from infection by the pathogen. A protective immune response can be measured, for example, by the inhibition of viral replication or plaque formation in a plaque reduction assay or ELISA-neutralization assay, or by measuring resistance to pathogen challenge in vivo. Exposure of a subject to an immunogenic stimulus, such as a pathogen or antigen (e.g., formulated as an immunogenic composition or vaccine), elicits a primary immune response specific for the stimulus, that is, the exposure "primes" the immune response. A subsequent exposure, e.g., by immunization, to the stimulus can increase or "boost" the magnitude (or duration, or both) of the specific immune response. Thus, "boosting" a preexisting immune response by administering an immunogenic composition increases the magnitude of an antigen (or pathogen) specific response, (e.g., by increasing antibody titer and/or affinity, by increasing the frequency of antigen specific B or T cells, by inducing maturation effector function, or any combination thereof).

The term "reduces" is a relative term, such that an agent reduces a response or condition if the response or condition is quantitatively diminished following administration of the agent, or if it is diminished following administration of the agent, as compared to a reference agent. Similarly, the term "protects" does not necessarily mean that an agent completely eliminates the risk of an infection or disease caused by infection, so long as at least one characteristic of the response or condition is substantially or significantly reduced or eliminated. Thus, an immunogenic composition that protects against or reduces an infection or a disease, or symptom thereof, can, but does not necessarily prevent or eliminate infection or disease in all subjects, so long as the incidence or severity of infection or incidence or severity of disease is measurably reduced, for example, by at least about 50%, or by at least about 60%, or by at least about 70%, or by at least about 80%, or by at least about 90% of the infection or response in the absence of the agent, or in comparison to a reference agent.

A "subject" is a living multi-cellular vertebrate organism. In the context of this disclosure, the subject can be an experimental subject, such as a non-human animal (e.g., a mouse, a rat, or a non-human primate). Alternatively, the subject can be a human subject.

The terms "derived from" or "of" when used in reference to a nucleic acid or protein indicates that its sequence is identical or substantially identical to that of an organism of interest.

The terms "decrease," "reduce" and "reduction" as used in reference to biological function (e.g., enzymatic activity, production of compound, expression of a protein, etc.) refer to a measurable lessening in the function by preferably at least 10%, more preferably at least 50%, still more preferably at least 75%, and most preferably at least 90%. Depending upon the function, the reduction may be from 10% to 100%. The term "substantial reduction" and the like refers to a reduction of at least 50%, 75%, 90%, 95% or 100%.

The terms "increase," "elevate" and "elevation" as used in reference to biological function (e.g., enzymatic activity, production of compound, expression of a protein, etc.) refer to a measurable augmentation in the function by preferably at least 10%, more preferably at least 50%, still more preferably at least 75%, and most preferably at least 90%. Depending upon the function, the elevation may be from 10% to 100%; or at least 10-fold, 100-fold, or 1000-fold up to 100-fold, 1000-fold or 10,000-fold or more. The term "substantial elevation" and the like refers to an elevation of at least 50%, 75%, 90%, 95% or 100%.

The terms "isolated" and "purified" as used herein refers to a material that is removed from at least one component with which it is naturally associated (e.g., removed from its original environment). The term "isolated," when used in reference to a recombinant protein, refers to a protein that has been removed from the culture medium of the bacteria that produced the protein. As such an isolated protein is free of extraneous compounds (e.g., culture medium, bacterial components, etc.).

EXAMPLES

Abbreviations: Ab (antibody); AGScAg (arctic ground squirrel hepadnavirus core antigen); BSA (bovine serum albumin); ELISA (enzyme-linked immunosorbent assay); GScAg (ground squirrel hepadnavirus core antigen); HBcAg (human hepatitis B virus core antigen); (hAg) heterologous antigen; MAb (monoclonal antibody); Mal (malaria); OD (optical density); PBS (phosphate buffered saline); VLP (virus-like particle); and WHcAg (woodchuck hepadnavirus core antigen).

Example 1—Deletion of Endogenous WHcAg B Cell Epitopes

General Methods

Construction and Expression of Recombinant Hybrid WHcAg Particles.

The woodchuck hepadnavirus genome has previously been described (Cohen et al., Virology, 162:12-20, 1998), GENBANK Accession No. NC_004107 (SEQ ID NO:16). Full length WHcAg (188 amino acids) was expressed from the pUC-WHcAg vector under the control of the Lac operon promoter. Epitope insert sequences were either designed to contain unique enzyme restriction sites, or overlapping oligonucleotides were designed to insert the sequence into the pUC-WHcAg vector. For the insert-fused and the insert-replacement sequences, insertion was achieved by PCR using overlapping oligonucleotides. For VLPs inserted at position 74, an existing SacI restriction site was used. For VLPs inserted at positions other than 74, the restriction sites EcoRI and XhoI were used, which resulted in the inclusion of N-terminal and C-terminal linkers flanking the heterologous polypeptide insert. Thus, the standard linker combination of the VLPs of the present disclosure is GILE-Xn-L, where Xn is an insert, X is any amino acid, and n is 50 or less (SEQ ID NO:17). C-terminal fusion was achieved by adding the EcoRV restriction site, which adds aspartic acid and isoleucine at the junction. N-terminal fusion was achieved by adding an NcoI restriction site upstream of the WLWG linker (SEQ ID NO:8).

Some of the hybrid WHcAg-RSV VLPs were constructed on full length (SEQ ID NO:1) or truncated WHcAg cores (SEQ ID NO:2), while others were constructed on full length or truncated WHcAg cores comprising modifications. Some WHcAg modifications were previously described in U.S. Pat. No. 7,320,795. Other WHcAg modifications were made so as to reduce carrier-specific antigenicity, and include: Δ2-WHcAg, Δ3-WHcAg, Δ4-WHcAg, Δ5-WHcAg, Δ6-WHcAg, Δ6.1-WHcAg, Δ7-WHcAg, and Δ7.1-WHcAg (described above in Table I).

Plasmids were transformed into chemically competent DH5alpha host cells according to standard protocols. The bacteria were grown overnight then lysed in a lysozyme-salt solution and clarified by centrifugation at 20,000×G for 30 min. The resulting supernatant was precipitated overnight in the cold with 25% ammonium sulfate. Lysates were screened in capture enzyme-linked immunosorbent assays (ELISAs) designed to assess three VLP properties: 1) protein expression of the WHcAg polypeptide by use of the 2221 MAb (Institute for Immunology, Tokyo University, Japan) specific for an epitope within residues 129 to 140 of WHcAg; 2) particle assembly using an antibody specific for a conformational epitope on WHcAg; and 3) display of the epitope of heterologous antigen (hAg) by use of hAg-reactive antibodies. The capture antibody was peptide-specific and noncompetitive with the detecting antibodies. The constructs that were positive for all three properties were selected for further purification on hydroxyapatite followed by gel filtration chromatography on SEPHAROSE 4B columns. The size of each hybrid WHcAg-hAg protein was confirmed by SDS-PAGE and western blotting.

Mouse Immunization.

For immunogenicity testing, B10×B10.S F1 mice were immunized intraperitoneally with 20 ug of VLP emulsified in IFA and boosted at week 8 with 10 ug in IFA. Mice were bled at week 8 after the primary immunization and again at 8 weeks post-boost.

ELISA Assay.

High binding ELISA plates (Costar) were coated overnight with 10 ug/ml peptide or 1 ug/ml of VLP or recombinant protein. Plates were blocked with 3% BSA in PBS. Five-fold dilutions of mouse anti-sera or MAb were applied to the plates for 1 hr. After 4 washes in 0.5% Tween 20, PBS, HRP-conjugated secondary anti-mouse IgG Ab diluted 1:5000 was applied for 1 hr. After washing, color was developed with 100 uL per well tetramethylbenzidine (Sigma). The reaction was stopped by addition of 100 per well 0.1 N HCl and optical density (OD) at 450 nm was read on an ELISA plate reader.

Δ1 Mutation of WHcAg

Although the purpose of Δ1 mutations was to insert heterologous antigens (hAg) comprising a B cell epitope (and/or T cell epitope) into WHcAg, such insertions can also reduce WHcAg-specific antigenicity. This is especially true when hAg are inserted within the immunodominant loop of WHcAg extending from residues 76 to 82 of SEQ ID NO:1 (Billaud et al., J Virol, 79:13641-13655, 2005). The immunodominant loop of WHcAg was defined in part by inference from the mapping of endogenous B cell epitopes on HBcAg (Milich et al., Vaccine 20:771-788, 2001; Belnap et al., Proc Natl Acad Sci USA, 100:10884-10889, 2003; and Harris et al., J Mol Biol, 355:562-576, 2006).

Δ2 Mutation of WHcAg

Residues 21-31 of HBcAg have been identified as partially representing an HBcAg-specific epitope defined by several Mabs, including Mab 3120 (Belnap et al., Proc Natl Acad Sci USA, 100:10884-10889, 2003). As determined during development of the present disclosure, replacing the HBcAg21-31 region with the WHcAg21-31 region in HBcAg allowed for VLP assembly without MAb 3120 binding (Table 1-1). MAb 3120 did recognize WHcAg, however, after replacing the WHcAg21-31 region with the HBcAg21-31 region in WHcAg. Reciprocally, HBcAg substituted with the WHcAg21-31 sequence was recognized by MAb 6D10, which did not recognize native HBcAg. Therefore, the WHcAg21-31 site represents an endogenous B cell site on WHcAg.

The Δ2 mutation, designated WHc (A21-31), focused on the 21-31 region of WHcAg by substituting alanine residues for WHcAg residues 21, 26, 27, 28, 29, and 31, which are the non-conserved residues between the WHcAg and the HBcAg. Neither the HBcAg-specific MAb 3120 nor one of the WHcAg-specific MAbs from our panel (6 D10, which is specific for WHcAg21-31), recognized WHc(A21-31) efficiently (Table 1-1). In addition to MAb 6D10, the Δ2 mutation significantly eliminated the binding of several other (1F10, 5A10) WHcAg-specific MAbs to WHcAg and to WHcAg-containing heterologous B cell inserts. It is noteworthy that MAb 6D10 bound efficiently to HBcAg (W21-31) yet not to HBcAg, thereby mapping the specificity of Mab 6D10 to the WHcAg21-31 region. MAbs 1F10 and 5A10 require the WHcAg21-31 region for binding, but the WHcAg21-31 region alone is not sufficient because these MAbs did not bind HBcAg (W21-31).

TABLE 1-1

Monoclonal Antibody Binding to
Chimeric Hepadnavirus Core Antigens

| Core VLPs | 6D10 MAb | 1F10 MAb | 5A10 MAb | 3120 MAb |
|---|---|---|---|---|
| WHcAg | ++ | ++ | ++ | 0 |
| HBcAg | 0 | 0 | 0 | ++ |
| HBcAg(W21-31) | ++ | 0 | 0 | 0 |
| WHcAg(H21-31) | 0 | 0 | 0 | ++ |
| WHcAg(A21-31) | 0 | 0 | 0 | 0 |

The majority of the anti-WHcAg MAb panel recognized hybrid WHcAgs containing heterologous antigens (e.g., foreign B cell epitope insertions), as well as native WHcAg (Table 1-2). MAb 13B5 was the only exception as it appeared to have required native WHcAg structure since this Ab almost exclusively recognized native WHcAg, but not any of the hybrid-WHcAg particles (Table 1-2) or numerous mutated hybrid-WHcAg particles (Table 1-3). The other seven anti-WHcAg MAbs made up an exemplary panel to screen how mutations Δ2-Δ7 affected the antigenicity and/or immunogenicity of hybrid-WHcAgs apart from the effect of insertion of heterologous antigens (Δ1). The hybrid-WHcAg particles listed in Table 1-2 contained heterologous epitopes from a variety of pathogens such as malaria (Mal), human hepatitis B virus (HBV), respiratory syncytial virus (RSV), anthrax (e.g., LF toxin, influenza A (e.g., IM2), and human immunodeficiency virus (HIV). These heterologous antigens were inserted in a variety of positions within WHcAg (e.g., positions 72, 74, 78, and 81). For example, two malaria-specific B cell epitopes were inserted within the loop region of a WHc(A21-31) particle to construct WHc(A21-31)-Mal-78. The effect of compromising two WHcAg regions on both antigenicity and immunogenicity was assessed as shown in FIG. 3A-FIG. 3D.

TABLE 1-2

Anti-WHcAg Monoclonal Antibody Recognition of VLPs as a Ratio of OD Values of Epitope-Inserted Plus Carrier-Mutated WHcAgs to Native WHcAg

| WHcAg Hybrid | MAB | | | | | | | Polyclonal α-WHc |
|---|---|---|---|---|---|---|---|---|
| | 6D10 | 4H11 | 1F10 | 1A12 | 13B5 | 1A9 | 15F1 | |
| WHc-Mal-78 | 1.0 | — | 0.2 | 0.46 | 0 | 1.0 | 0.41 | — |
| WHc-Mal5-78 | 1.2 | 1.3 | 1.1 | 0.49 | 0 | 0.91 | 0.47 | 0.12 |
| WHc-Mal-78-UTC | 1.2 | 0.9 | 0.8 | 0.59 | 0 | 0.86 | 0.51 | 0.23 |
| WHc-Mal-78-TH | 0.9 | 1.1 | 0.8 | 0.29 | 0 | 0.91 | 0.26 | 0.09 |
| WHc-HBV1.6-78 | 1.0 | 0.94 | 0.87 | 0.4 | 0 | 1.0 | 0.47 | 0.21 |
| WHc-RSV10-78 | 1.7 | — | 0.86 | 0.68 | 0 | 0.84 | 1.0 | — |
| WHc-LF-78 | 1.0 | 0.88 | 0.93 | 0.61 | 0 | 0.89 | 0.38 | 0.23 |
| WHc-IM2-81 | 1.7 | — | 0.53 | 1.1 | 0 | 0.87 | 1.3 | — |
| WHc-HIV5.1-72 | 2.0 | — | 0.27 | 0.6 | 0 | 0.87 | 0.93 | — |

TABLE 1-2-continued

Anti-WHcAg Monoclonal Antibody Recognition of VLPs as a Ratio of OD Values of Epitope-Inserted Plus Carrier-Mutated WHcAgs to Native WHcAg

| WHcAg Hybrid | MAB | | | | | | | Polyclonal α-WHc |
|---|---|---|---|---|---|---|---|---|
| | 6D10 | 4H11 | 1F10 | 1A12 | 13B5 | 1A9 | 15F1 | |
| Native WHcAg (O.D.) | 0.7 | 1.7 | 1.5 | 0.9 | 1.1 | 1.1 | 0.86 | 1.3 |

Figure 3:
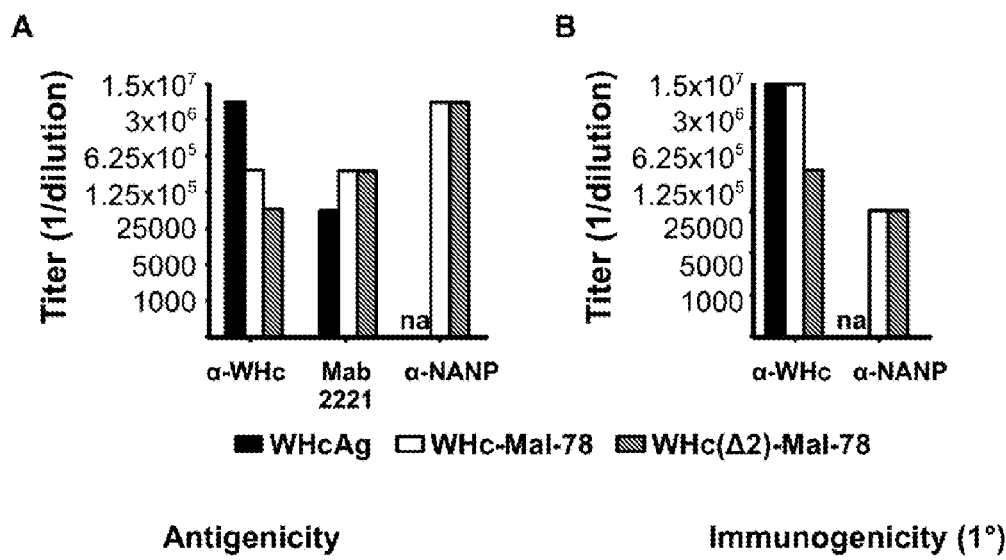
FIG. 3A shows the antigenicity of wild type, hybrid, and modified hybrid WHcAg cores. The wild type WHcAg, hybrid WHc-Mal-78 (WHcAg with malaria B cell epitopes inserted at residue 78 of the immunodominant loop), and hybrid WHc(A21-31)-Mal-78 (delta2 WHcAg with malaria B cell epitopes inserted at residue 78 of the immunodominant loop) were tested by ELISA for binding of an anti-WHcAg polyclonal sera, an anti-WHcAg peptide monoclonal (Mab 2221) and an anti-NANP monoclonal antibody. The malarial amino acid sequence (heterologous polypeptide) of the hybrid cores is set forth as SEQ ID NO:14.
FIGS. 3B, 3C and 3D show the immunogenicity of wild type, hybrid, and modified hybrid WHcAg cores. WHcAg, WHc-Mal-78, and WHc(A21-31)-Mal-78 were injected (20 µg, IFA) into mice and anti-WHc and anti-malaria antibody titers were determined by ELISA four weeks post-immunization (primary), and at 16 weeks post-boost (secondary).

Antigenicity analysis of the double (Δ1+Δ2) mutant WHc(A21-31)-Mal-78 particle revealed that it bound a polyclonal anti-WHcAg antisera 120-fold less efficiently than the wild type WHcAg and 5-fold less efficiently than a single (Δ1) mutant WHcAg-Mal-78. Binding of a WHcAg peptide-specific Mab (2221) and a NANP-specific Mab (2A10) to WHc(A21-31)-Mal-78 and WHc-Mal-78 were equivalent (FIG. 3A). In an immunogenicity experiment, the antibody titers at 4 weeks, after one immunization showed that mutating the B cell epitope in the 21-31 region of WHc(A21-31)-Mal-78 reduced anti-WHcAg antibody production 120-fold in comparison to WHcAg and to WHc-Mal-78, but did not affect anti-NANP (e.g., Mal insert) antibody production (FIG. 3B). Upon secondary immunization, the anti-NANP and anti-NVDP insert titers elicited by the WHc(A21-31)-Mal-78 (Δ1 and Δ2) mutant actually increased by 25-fold as compared to the WHcAg-Mal-78 particle (FIG. 3C-FIG. 3D). Therefore, deleting a WHcAg carrier-specific B cell epitope positively affected the anti-insert immune response as a direct or indirect consequence of reducing the anti-WHcAg antibody response.

TABLE 1-3

Anti-WHcAg Monoclonal Antibody Recognition of VLPs as a Ratio of OD Values of Epitope-Inserted Plus Carrier-Mutated WHcAgs to Native WHcAg

| Mutated WHcAgs | MAB | | | | | | | Polyclonal α-WHc |
|---|---|---|---|---|---|---|---|---|
| | 6D10 | 4H11 | 1F10 | 1A12 | 13B5 | 1A9 | 15F1 | |
| WHc(A21-31) = Δ2 | | | | | | | | |
| WHc(A21-31)-Mal-78 | 0.11 | — | 0.02 | 0.14 | 0 | 0.85 | 0.16 | — |
| WHc(A2131-C61S)-Mal-78 | 0.21 | 1.1 | 0.38 | 0 | 0 | 0.53 | 0.63 | 0.15 |
| WHc(N136P/A137P) = Δ3 | | | | | | | | |
| WHc(N136P/A137P)-Mal-78 | 0.51 | 0.50 | 0.3 | 0.22 | 0 | 0.35 | 0.30 | 0.08 |
| WHc(A21-31, N136P/A137P)-Mal-78 | 0.03 | — | 0.01 | 0.02 | 0 | 0.46 | 0.15 | — |
| WHc(C61S) = Δ4 | | | | | | | | |
| WHc(C61S)-HBV1.6-78 | 0.74 | 0.76 | 0.73 | 0.14 | 0 | 0.75 | 0.27 | 0.19 |
| WHc(C61S)-Mal5-78 | 0.64 | 0.76 | 0.60 | 0 | 0 | 0.68 | 0.21 | 0.09 |
| WHc(C61S)-Mal-78-UTC | 0.39 | 0.59 | 0.22 | 0 | 0 | 0.37 | 0 | 0 |
| WHc(C61S)-RSV1-78 | 0.76 | 0.65 | 0.54 | 0.11 | 0 | 0.62 | 0.48 | 0.13 |
| WHc(C61S)-LF375-78 | 0.81 | 0.83 | 0.55 | 0.16 | 0 | 0.58 | 0.62 | 0.16 |
| WHc(C61S)-HBV1.3(+)-78 | 0.69 | 0.59 | 0.73 | 0 | 0 | 0.66 | 0.33 | 0.16 |
| WHc(replace aa62-89) = Δ5 | | | | | | | | |
| WHc(Δ62-85)-RSV1 | 0.49 | 0.71 | 0.36 | 0 | 0 | 0.55 | 0.28 | 0 |
| WHc(Δ64-87)-RSV5 | 0.51 | 0.76 | 0.47 | 0 | 0 | 0.62 | 0.3 | 0.1 |
| WHc(Δ65-88)-RSV1 | 0.57 | 0.58 | 0.40 | 0 | 0 | 0.42 | 0.23 | 0 |
| WHc(A → R motifs) = Δ6 | | | | | | | | |
| WHc(A → R)-Mal-Ct | 1.7 | — | 0.01 | 0.29 | 0.23 | 0.46 | 0.33 | — |
| WHc(75-83Δ) = Δ7 | | | | | | | | |
| WHc(A75-83) | 0.89 | 1.0 | 1.0 | 1.1 | 0 | 1.0 | 0.77 | 0.35 |
| WHc(A75-83)-Mal-74 | 1.4 | — | 0.35 | 1.1 | 0 | 1.4 | 0.73 | — |

Δ3 Mutation of WHcAg

The 120-140 region of HBcAg has been thought to contain B cell epitopes largely in denatured HBcAg (Pushko et al., Virology, 202:912-920, 1994; Isaguliants et al., Biochemistry (Mosc) 63:551-8, 1993; and Bichko et al., Mol Immunol, 30:221-23, 1993). When mice were immunized with the WHc(A21-31)-Mal-78 mutant (Δ1 and Δ2) particle, high levels of antibody specific for the WHcAg129-140 region was produced. The fine specificity of this anti-WHc129-140 antibody was mapped using alanine analogs at each amino acid position. As shown in Table 1-4) anti-WHcAg129-140 binding activity was significantly reduced by single alanine substitutions at residues 133, 134, and 138 and abolished by a single alanine substitution at residue 136 and a single phenylalanine substitution at residue 137. This data maps the WHcAg129-140 B cell epitope to residues 133-138 with the most important antibody contact sites at N136 and A137.

TABLE 1-4

Mapping of a B cell epitope to WHcAg Residues 133-138

| WHcAg | Sequence | SEQ ID NO | Anti-WHc(A21-31)-Mal78 (OD) |
|---|---|---|---|
| wt | P P A Y R P P N A P I L | | 1.30 |
| 129 | A – – – – – – – – – – – | | 1.30 |
| 130 | – A – – – – – – – – – – | | 1.30 |
| 131 | – – F – – – – – – – – – | | 0.60 |
| 132 | – – – A – – – – – – – – | | 0.80 |
| 133 | – – – – A – – – – – – – | | 0.05 |
| 134 | – – – – – A – – – – – – | | 0.06 |
| 135 | – – – – – – A – – – – – | | 0.24 |
| 136 | – – – – – – – A – – – – | | 0 |
| 137 | – – – – – – – – F – – – | | 0 |
| 138 | – – – – – – – – – A – – | | 0.04 |
| 139 | – – – – – – – – – – A – | | 0.20 |
| 140 | – – – – – – – – – – – A | | 0.60 |
| Δ3 mutant | P P A Y R P P P P P I L | | |

In order to delete or reduce the antigenicity of residues 133-138 on WHcAg, N136 and A137 were replaced with prolines, thereby converting the WHcAg134-138 sequence to a contiguous stretch of five prolines. As shown in Table 1-3, recognition of the Δ3 mutant WHcAg (N136P/A137P)-Mal78 particle was significantly reduced as compared to native WHcAg by MAbs 1F10, 1A12, 13B5, 1A9, and 15F1, as well as by a polyclonal anti-WHcAg antiserum. An at least 50% reduction in a Mab binding to a mutant particle as compared to Mab binding to the native WHcAg was considered to be a significant reduction in antigenicity of the mutant (e.g., binding ratio <0.5).

Δ4 Mutation of WHcAg

The Δ4 mutation is a single substitution of serine for cysteine at position 61 (C61S). As shown in FIG. 1A, cysteine at this position is conserved in multiple mammalian hepadnavirus core antigens. Although Cys61 is required for antigenicity of the secreted HBeAg, the C61S substitution on full-length HBcAg does not affect HBcAg functions such as particle formation, pre-genome packaging, or DNA replication (Nassal et al., Virology, 190:499-505, 1992) nor does it affect HBcAg antigenicity for several anti-HBc Mabs. The Cys61 requirement for HBeAg antigenicity is thought to be due in part to the precore Cys7-core Cys61 disulfide bond that prevents assembly of HBeAg dimers (Nassal et al., J Virol, 67:4307-4315, 1993; Bang et al., Virology, 332:216-224, 2004; and Wasenauer et al., J Virol, 67:1315-1321, 1993). Nevertheless, because the cysteine at residue 61 on monomers of HBcAg and WHcAg form disulfide bonds (Cys61-Cys61), which may stabilize the dimer, it was of interest to determine if the lack of Cys61 on WHcAg would affect the antigenicity of hybrid WHcAg particles harboring heterologous B cell epitopes.

As shown in Table 1-3, the antigenicity of a number of WHcAg-hybrid particles containing the C61S substitution (Δ4 mutation) was significantly reduced. Recognition of Δ4-mutated WHcAg-hybrid particles by Mabs 1A12, 13B5, and 15F1 as compared to native WHcAg were particularly negatively affected (Table 1-3). Immunogenicity tests with hybrid WHcAg-hAg particles carrying the C61S substitution (Δ4 mutation) revealed reduced anti-WHcAg (carrier-specific) antibody production and/or increased anti-insert antibody production, as shown in Table 1-5.

TABLE 1-5

Immunogenicity of Hybrid, WHcAg-hAg VLPs Δ2-Δ7 Mutants as Compared to a Δ1 Mutant

| | | Titer (1/dilution) | |
|---|---|---|---|
| WHcAg Hybrid | mutation | Anti-WHc | Anti-Insert |
| WHcRSV1-78 | Δ1 only | 15 × 10⁶ | 125,000 |
| WHc(C61S)-RSV1-78 | Δ1 + Δ4 | 625,000 | 125,000 |
| WHc-Mal5-78 | Δ1 only | 1.2 × 10⁶ | 625,000 |
| WHc(C61S)-Mal-78 | Δ1 + Δ4 | 250,000 | 625,000 |
| WHc(A21-31, N136P/A137P)-Mal-78 | Δ1 + Δ2 + Δ3 | 125,000 | 3 × 10⁶ |
| WHc-HBV1.3-78 | Δ1 only | 625,000 | 125,000 |
| WHc(C61S)-HBV1.3(+)-78 | Δ1 + Δ4 | 125,000 | 3 × 10⁶ |
| WHc-HBV1.6-78 | Δ1 only | 125,000 | 125,000 |
| WHc(C61S)-HBV1.6-78 | Δ1 + Δ4 | 125,000 | 625,000 |

Δ5 Mutation of WHcAg

Most heterologous epitopes are inserted between WHcAg amino acids within the loop domain (76-82) due to enhanced immunogenicity of these positions as compared to N-terminal or C-terminal positions (Billaud et al., J Virol, 79:13656-13666, 2005; and Schodel et al., J Virol, 66:106-114, 1992). However, a low percentage of heterologous epitopes inserted into the loop domain of WHcAg, especially those composed of alpha-helical structures, may not permit assembly, may not elicit high levels of anti-insert antibodies, and/or may not elicit functional anti-insert antibodies, possibly due to structural constraints in the context of the WHcAg-hAg fusion protein (Roseman et al., J Mol Biol, 423:63-78, 22, 2012; and Brown et al., Vaccine, 9:595-601, 1991). One method to mitigate structural constraints imparted to the heterologous insert is to replace WHcAg sequence that is structurally similar (e.g., comparable secondary structure) to the heterologous antigen, with the heterologous antigen rather than simply inserting the heterologous antigen at a defined WHcAg position. In the case of the Δ5 mutation, this involved replacing WHcAg residues 62-85, or 65-88 with a 24 residue heterologous antigen derived from the RSV F protein [WHc(Δ62-85)-RSV-1 or WHc(Δ65-88)-RSV-1], respectively. Another Δ5 mutation replaced WHcAg residues 64-87 with a 22 residue heterologous antigen derived from the RSV-F protein (WHc(Δ64-87)-RSV-5). In addition to effects on the inserted B cell epitopes, all three Δ5 mutations had significant effects on the binding of Mabs 1A12, 13B5, and 15F1 and lesser effects on the binding of Mab1F10 as compared to their binding to native WHcAg (Table 1-3).

Immunogenicity studies demonstrated that in addition to reducing WHcAg antigenicity, the WHc(Δ65-88)-RSV-1 particle elicited significantly more RSV-neutralizing antibodies (i.e., 1:537 endpoint dilution titer) than did the WHc-RSV-1-78 particle (i.e., 1:141 endpoint dilution titer), in which the same 24 residue RSV-F protein sequence was simply inserted into WHcAg at position 78. Furthermore, combining the Δ5 mutation and the Δ4 mutation on a single particle, such as WHc(Δ65-88)(Cys61→S)-RSV-1, further increased neutralizing antibody production to an endpoint dilution titer of 1:5887. This is another example of WHcAg-specific mutations designed to reduce WHcAg antigenicity also having positive effects on the immune response to the heterologous antigen. This example also demonstrates that Δ1, Δ4, and Δ5 WHcAg mutations can be combined on a single hybrid-WHcAg particle. Other examples of the effects of combining WHcAg Δ mutations on antigenicity (e.g., Mab recognition) are shown in Table 16. In all the comparisons between hybrid-WHcAg particles harboring a single WHcAg mutation versus double WHcAg mutations, the two mutation hybrid WHcAg-hAg particles were less antigenic in terms of binding one or more Mabs (Table 1-6).

WHcAg particle carrying a malaria epitope at the C-terminus. The arginines at positions 156 and 159 were also substituted with alanines. As shown in Table 1-3, the Δ6 mutation had a dramatic and unexpected effect on WHcAg antigenicity. All WHcAg-specific Mabs, except Mab 6D10, bound to the Δ6 mutant very poorly or not at all. Presumably, the absence of the four arginine-rich motifs altered the structure of the hybrid-WHcAg particles sufficiently to affect most of the endogenous WHcAg-specific B cell epitopes.

Immunogenicity testing of WHc (Ala→R)-Mal-Ct also revealed an interesting result as shown in Table 1-7). As predicted by the reduced WHcAg-antigenicity of the WHc (Ala→R)-Mal-Ct particle, primary and secondary anti-WHc antibody production was reduced 24-fold and 14-fold, respectively, after immunization with the Δ6 mutant as compared to the WHc-Mal-Ct particle. The reduced anti-WHcAg responses were also reflected in significantly lower antibody responses to two linear C-terminal peptide epitopes on WHcAg (i.e., W140-155 and W155-175) upon immunization with the Δ6 mutant as compared to WHc-Mal-Ct. However, the Δ6 mutation had the opposite effect on the anti-malaria antibody responses, which increased after immunization with the WHc(Ala→R)-Mal-Ct particle as compared to the WHc-Mal-Ct particle (Table 1-7).

Adding heterologous B cell epitopes to the C-terminus of WHcAg and HBcAg is known to result in relatively low

TABLE 1-6

Effect of Combining WHcAg Mutations on Monoclonal Antibody Recognition

| WHcAg Hybrid | Mutations | Mab (O.D.) | | | | | | |
|---|---|---|---|---|---|---|---|---|
| | | 4H11 | 1A9 | 1F10 | 6D10 | 13B5 | 1A12 | 15F1 |
| WHc(Δ64-87)-RSV5 | Δ5 | 0.48 | 0.39 | 0.43 | 0.35 | 0 | 0 | 0.45 |
| WHc(C61S, Δ64-87)-RSV5 | Δ4 + Δ5 | 0.08 | 0.05 | 0.09 | 0.41 | 0 | 0 | 0.46 |
| WHc(N136P/A137P)-Mal-78 | Δ3 | 0.84 | 0.38 | 0.45 | 0.36 | 0 | 0.2 | 0.25 |
| WHc(A21-31, N136P/A137P)-Mal-78 | Δ2 + Δ3 | 0.75 | 0.51 | 0.01 | 0.02 | 0 | 0.02 | 0.12 |
| WHc(Δ62-85)-RSV1 | Δ5 | 0.6 | 0.45 | 0.47 | 0.3 | 0 | 0 | 0.39 |
| WHc(C61S, Δ62-85)-RSV1 | Δ4 + Δ5 | 0.22 | 0.13 | 0.2 | 0.46 | 0 | 0 | 0.62 |

Δ6 Mutation of WHcAg

WHcAg possesses four arginine-rich motifs at the C-terminus. Specifically, RRR150-152, RRR162-64, RRR169-171, and RRRR177-180. These arginine-rich motifs are involved in binding pre-genomic RNA and also serve as nuclear membrane localization signals. The arginine-rich motifs also bind host ssRNA when recombinant WHcAg is expressed in a bacterial or yeast cell. In order to abrogate ssRNA binding, WHcAg was mutated (Δ6) by introduction of multiple R/A substitutions encompassing the four arginine-rich motifs (WHc (Ala→R)-Mal-Ct) on a hybridanti-insert antibody production (Schodel et al., J Virol, 66:106-114, 1992). Without being bound by theory, this may be due to poor exposure of the added epitopes at the C-terminus due to internalization of this region together with the encapsidation of nucleic acid. Removal of the arginine-rich motifs and the subsequent absence of ssRNA within the Δ6 mutant particle are thought to reduce the internalization of the C-terminal malaria epitopes. Thus, the Δ6 mutation is useful for presenting heterologous B cell epitopes at the C-terminus of WHcAg, as well as for reduction of WHcAg-specific antigenicity.

TABLE 1-7

Effect of R/A Substitutions in WHcAg (Δ6 mutant) on Immunogenicity

| WHcAg Hybrid | Dose | Antibody Titer (1/dilution) | | | | | |
|---|---|---|---|---|---|---|---|
| | | WHcAg | $W_{140-155}$ | $W_{140-155}$ | NANP | NVDP | rCSP |
| WHcMal-Ct | 1° | $3 \times 10^6$ | 5,000 | 1,000 | 0 | 0 | 1,000 |
| | 2° | $9 \times 10^6$ | 50,000 | 125,000 | 1,000 | 0 | 5,000 |
| WHc-(A→R)-Mal-Ct | 1° | 125,000 | 0 | 0 | 25,000 | 5,000 | 25,000 |
| | 2° | 650,000 | 1,000 | 2,000 | 250,000 | 250,000 | 625,000 |

Δ7 Mutation of WHcAg

The loop domain (76-82) of WHcAg/HBcAg contains the immunodominant region and is localized at the tip of the protruding spikes displayed over the surface. Heterologous B cell epitopes are frequently inserted within this loop domain so as to enhance foreign epitope exposure, antigenicity and immunogenicity (Schodel et al., J Virol, 66:106-114, 1992). As shown in Table 1-3, effective deletion of the loop region by replacement with nine contiguous alanine residues as in WHc(Δ75-83), reduced antigenicity as measured by loss of Mab 13B5 binding and reduced binding by the polyclonal anti-WHcAg antisera. The polyclonal anti-WHcAg antisera was an early primary bleed of WHcAg-immunized Balb/c mice and was designed to be enriched in structurally-dependent and loop region-specific antibodies. The 13B5 Mab appeared to also be highly dependent on native WHcAg structure and loop-specific, since it did not bind the WHcAg mutant particles. Furthermore, 13B5 does not bind ground squirrel or arctic ground squirrel core particles (Table II), which are highly similar to WHcAg except within the loop regions (Billaud et al., J Virol, 79:13641-13655, 2005; and Billaud et al., Vaccine, 25:1593-1606, 2007). The other WHcAg-specific Mabs are less dependent on native WHcAg structure. This may be due in part because the Mab panel was selected on both native WHcAg and hybrid-WHcAg particles to select for WHcAg-specific antibodies that recognize epitopes expressed on hybrid-WHcAg particles.

A co-pending U.S. provisional patent application referred to as U.S. Appl. Ser. No. 61/802,240 is hereby incorporated by reference in its entirety. In particular, the sequences of (U.S. Provisional Application No. 61/802,240, filed Mar. 15, 2013), are hereby incorporated by reference.

```
SEQUENCES
                                                         SEQ ID NO: 1
>WHcAg full length
MDIDPYKEFGSSYQLLNFLPLDFFPDLNALVDTATALYEEELTGREHCSPHHTAIRQALVCWDELTKLIA

WMSSNITSEQVRTIIVNHVNDTWGLKVRQSLWFHLSCLTFGQHTVQEFLVSFGVWIRTPAPYRPPNAPIL

STLPEHTVIRRRGGARASRSPRRRTPSPRRRRSQSPRRRRSQSPSANC

SEQ ID NO: 2
>WHcAg Δ2
MDIDPYKEFGSSYQLLNFLPADFFPAAAVLADTATALYEEELTGREHCSPHHTAIRQALVCWDELTKLIA

WMSSNITSEQVRTIIVNHVNDTWGLKVRQSLWFHLSCLTFGQHTVQEFLVSFGVWIRTPAPYRPPNAPIL

STLPEHTVIRRRGGARASRSPRRRTPSPRRRRSQSPRRRRSQSPSANC

SEQ ID NO: 3
>WHcAg Δ3
MDIDPYKEFGSSYQLLNFLPLDFFPDLNALVDTATALYEEELTGREHCSPHHTAIRQALVCWDELTKLIA

WMSSNITSEQVRTIIVNHVNDTWGLKVRQSLWFHLSCLTFGQHTVQEFLVSFGVWIRTPAPYRPPPPPIL

STLPEHTVIRRRGGARASRSPRRRTPSPRRRRSQSPRRRRSQSPSANC

SEQ ID NO: 4
>WHcAg Δ4
MDIDPYKEFGSSYQLLNFLPLDFFPDLNALVDTATALYEEELTGREHCSPHHTAIRQALVSWDELTKLIA

WMSSNITSEQVRTIIVNHVNDTWGLKVRQSLWFHLSCLTFGQHTVQEFLVSFGVWIRTPAPYRPPNAPIL

STLPEHTVIRRRGGARASRSPRRRTPSPRRRRSQSPRRRRSQSPSANC

SEQ ID NO: 5
>WHcAg Δ5
MDIDPYKEFGSSYQLLNFLPLDFFPDLNALVDTATALYEEELTGREHCSPHHTAIRQALVCXXXXXXXXX

XXXXXXXXXXXXXXXXXHVNDTWGLKVRQSLWFHLSCLTFGQHTVQEFLVSFGVWIRTPAPYRPPNAPIL

STLPEHTVIRRRGGARASRSPRRRTPSPRRRRSQSPRRRRSQSPSANC

SEQ ID NO: 6
>WHcAg Δ6
MDIDPYKEFGSSYQLLNFLPLDFFPDLNALVDTATALYEEELTGREHCSPHHTAIRQALVCWDELTKLIA

WMSSNITSEQVRTIIVNHVNDTWGLKVRQSLWFHLSCLTFGQHTVQEFLVSFGVWIRTPAPYRPPNAPIL

STLPEHTVIAAAGGAAASASPAAATPSPAAARSQSPAAAASQSPSANC

SEQ ID NO: 7
>WHcAg Δ7
MDIDPYKEFGSSYQLLNFLPLDFFPDLNALVDTATALYEEELTGREHCSPHHTAIRQALVCWDELTKLIA

WMSSAAAAAAAAAIIVNHVNDTWGLKVRQSLWFHLSCLTFGQHTVQEFLVSFGVWIRTPAPYRPPNAPIL

STLPEHTVIRRRGGARASRSPRRRTPSPRRRRSQSPRRRRSQSPSANC
```

```
                                                           SEQ ID NO: 8
>GScAg
MDIDPYKEFGSSYQLLNFLPLDFFPDLNALVDTAAALYEEELTGREHCSPHHTAIRQALVCWEELTRLIT

WMSENTTEEVRRIIVDHVNDTWGLKVRQTLWFHLSCLTFGQHTVQEFLVSFGVWIRTPAPYRPPNAPILS

TLPEHTVIRRGGSRAARSPRRRTPSPRRRRSQSPRRRRSQSPASNC

SEQ ID NO: 9
>AGScAg
MDIDPYKEFGSSYQLLNFLPLDFFPELNALVDTATALYEEELTGREHCSPHHTAIRQALVCWEELTRLIA

WMSANINSEEVRRVIVAHVNDTWGLKVRQNLWFHLSCLTFGQHTVQEFLVSFGVRIRTPAPYRPPNAPIL

STLPEHTVIRRRGSARVVRSPRRRTPSPRRRRSQSPRRRRQSPASNC

SEQ ID NO: 10
>HBcAg
MDIDPYKEFGATVELLSFLPSDFFPSVRDLLDTASALYREALESPEHCSPHHTALRQAILCWGELMTLAT

WVGVNLEDPASRDLVVSYVNTNMGLKFRQLLWFHISCLTFGRETVIEYLVSFGVWIRTPPAYRPPNAPIL

STLPETTVVRRRGRSPRRRTPSPRRRRSQSPRRRRSQSRESQC

SEQ ID NO: 11
>WHcAg truncated
MDIDPYKEFGSSYQLLNFLPLDFFPDLNALVDTATALYEEELTGREHCSPHHTAIRQALVCWDELTKLIA

WMSSNITSEQVRTIIVNHVNDTWGLKVRQSLWFHLSCLTFGQHTVQEFLVSFGVWIRTPAPYRPPNAPIL

STLPEHTVI

SEQ ID NO: 12
>WHcAg dB truncated (X is any amino acid or missing)
MDIDPYKEFG SSYQLLNFLP XDFFPXXXXL XDTATALYEE ELTGREHCSP HHTAIRQALV

XXXXXXXXXX XXXXXXXXXX XXXXXXXHVN DTWGLKVRQS LWFHLSCLTF GQHTVQEFLV

SFGVWIRTPA PYRPPXXPIL STLPEHTVIX XXXXXXXXXX XXXXXXXXXX XXXXXXXXXX

XXXXXXXX

SEQ ID NO: 13
>WHcAg dB full length (X is any amino acid or missing)
MDIDPYKEFG SSYQLLNFLP XDFFPXXXXL XDTATALYEE ELTGREHCSP HHTAIRQALV

XXXXXXXXXX XXXXXXXXXX XXXXXXXHVN DTWGLKVRQS LWFHLSCLTF GQHTVQEFLV

SFGVWIRTPA PYRPPXXPIL STLPEHTVIX XXGGAXASXS PXXXTPSPXX XRSQSPXXXX

SQSPSANC

SEQ ID NO: 14
>Malaria epitope
NANP NVDP NANP NANP NANP

SEQ ID NO: 15
>RSV F protein epitope
NSELLSLINDMPITNDQKKLMSNN

SEQ ID NO: 16
>WHV genome
   1 aattcgggac ataccacgtg gtttagttcc gcctcaaact ccaacaaatc gagatcaagg 61 gagaaagcct actcctccaa ctccacctct aagagatact caccccccact taactatgaa 121 aaatcagact tttcatctcc aggggttcgt agacggatta cgagacttga caacaacgga 181 acgccaacac aatgcctatg gagatccttt tacaacacta gccctgcgg ttcctactgt 241 atccaccata ttgtctcctc cctcgacgac tggggaccct gcactgtcac cggagatgtc 301 accatcaagt ctcctaggac tcctcgcagg attacaggtg gtgtatttct tgtggacaaa 361 aatcctaaca atagctcaga atctagattg gtggtggact tctctcagtt ttccagggg 421 cataccagag tgcactggcc aaaattcgca gttccaaact tgcaaacact tgccaacctc 481 ctgtccacca acttgcaatg gctttcgttg gatgtatctg cggcgtttta tcatatacct 541 attagtcctg ctgctgtgcc tcatcttctt gttggttctc ctggactgga aaggtttaat
```

-continued

```
 601 acctgtctgt cctcttcaac ccacaacaga acaacagtc aattgcagac aatgcacaat
 661 ctctgcacaa gacatgtata ctcctcctta ctgttgttgt ttaaaaccta cggcaggaaa
 721 ttgcacttgt tggcccatcc cttcatcatg ggctttagga aattacctat gggagtgggc
 781 cttagcccgt ttctcttggc tcaatttact agtgccctg cttcaatggt taggaggaat
 841 ttccctcatt gcgtggtttt tgcttatatg gatgatttgg ttttgggggc ccgcacttct
 901 gagcatctta ccgccattta ttcccatatt tgttctgttt ttcttgattt gggtatacat
 961 ttgaatgtca ataaaacaaa atggtggggc aatcatctac atttcatggg atatgtgatt
1021 actagttcag gtgtattgcc acaagacaaa catgttaaga aaatttcccg ttatttgcgc
1081 tctgttcctg ttaatcaacc tctggattac aaaatttgtg aaagattgac tggtattctt
1141 aactatgttg ctccttttac gctatgtgga tacgctgctt taatgccttt gtatcatgct
1201 attacttccc gtacggcttt cattttctcc tccttgtata atcctggtt gctgtctctt
1261 tatgaggagt tgtggcccgt tgtcaggcaa cgtggcgtgg tgtgcactgt gtttgctgac
1321 gcaacccccca ctggttgggg cattgccacc acctatcaac tccttccgg gactttcgct
1381 ttccccctcc ctattgccac ggcggaactc attgccgcct gccttgcccg ctgctggaca
1441 ggggctcggc tgttgggcac tgacaattcc gtggtgttgt cggggaagct gacgtccttt
1501 ccatggctgc tcgcctgtgt tgccaactgg attctgcgcg gacgtccttc ctgctacgtc
1561 ccttcggccc tcaatccagc ggaccttcct tcccgcggcc tgctgccggt tctgcggcct
1621 cttccgcgtc ttcgccttcg ccctcagacg agtcggatct cccttgggc cgcctccccg
1681 cctgtttcgc ctcggcgtcc ggtccgtgtt gcttggtctt cacctgtgca gaattgcgaa
1741 ccatggattc caccgtgaac tttgtctcct ggcatgcaaa tcgtcaactt ggcatgccaa
1801 gtaaggacct ttggactcct tatataaaag atcaattatt aactaaatgg gaggagggca
1861 gcattgatcc tagattatca atatttgtat taggaggctg taggcataaa tgcatgcgac
1921 ttctgtaacc atgtatcttt ttcacctgtg ccttgttttt gcctgtgttc catgtcctac
1981 ttttcaagcc tccaagctgt gccttggatg gctttggggc atggacatag atccctataa
2041 agaatttggt tcatcttatc agttgttgaa ttttcttcct ttggacttct ttcctgacct
2101 taatgctttg gtggacactg ctactgcctt gtatgaagaa gagctaacag gtagggaaca
2161 ttgctctccg caccatacag ctattagaca agctttagta tgctgggatg aattaactaa
2221 attgatagct tggatgagct ctaacataac ttctgaacaa gtaagaacaa tcatagtaaa
2281 tcatgtcaat gatacctggg gacttaaggt gagacaaagt ttatggttc atttgtcatg
2341 tctcactttt ggacaacata cagttcaaga atttttagta agttttggag tatggatcag
2401 aactccagct ccatatagac ctcctaatgc acccattctc tcgactcttc cggaacatac
2461 agtcattagg agaagaggag gtgcaagagc ttctaggtcc cccagaagac gcactccctc
2521 tcctcgcagg agaagatctc aatcaccgcg tcgcagacgc tctcaatctc catctgccaa
2581 ctgctgatct tcaatgggta cataaaacta atgctattac aggtctttac tctaaccaag
2641 ctgctcagtt caatccgcat tggattcaac ctgagtttcc tgaacttcat ttacataatg
2701 atttaattca aaaattgcaa cagtattttg gtcctttgac tataaatgaa aagagaaaat
2761 tgcaattaaa ttttcctgcc agattttccc ccaaagctac taaatatttc cctttaatta
2821 aaggcataaa aaacaattat cctaatttg ctttagaaca tttctttgct accgcaaatt
2881 atttgtggac tttatgggaa gctggaattt tgtatttaag gaagaatcaa acaactttga
2941 cttttaaagg taaaccatat tcttgggaac acagacagct agtgcaacat aatgggcaac
3001 aacataaaag tcaccttcaa tccagacaaa atagcagcat ggtggcctgc agtgggcact
```

-continued

```
3061 tattacacaa ccacttatcc tcagaatcag tcagtgtttc aaccaggaat ttatcaaaca 3121 acatctctga taaatcccaa aaatcaacaa gaactggact ctgttcttat aaacagatac 3181 aaacagatag actggaacac ttggcaagga tttcctgtgg atcaaaaatt accattggtc 3241 agcagggatc ctcccccaaa acctatata aatcaatcag ctcaaacttt cgaaatcaaa 3301 cctgggccta taatagttcc cgg
```

```
                                                SEQ ID NO: 17
>linker combination
GILE-Xn-L
where X is any amino acid, n is 60 or less SEQ ID NO: 18
>linker
WLWG
```

---

We claim:

1. An antigenic composition comprising a hybrid woodchuck hepadnavirus core antigen, wherein
    the hybrid core antigen is a fusion protein comprising a heterologous antigen and a woodchuck hepadnavirus core antigen comprising the amino acid sequence of SEQ ID NO:12 with a serine at position 61, and
    the fusion protein is capable of assembling as a hybrid virus-like particle (VLP).

2. The antigenic composition of claim 1, wherein the heterologous antigen is from 4 to 50 amino acids in length.

3. The antigenic composition of claim 2, wherein the heterologous antigen is inserted at a position within the core antigen selected from the group consisting of N-terminal, 44, 71, 72, 73, 74, 75, 76, 77, 78, 81, 82, 83, 84, 85, 92, 149 and C-terminal, as numbered according to SEQ ID NO:1.

4. The antigenic composition of claim 3, wherein the woodchuck hepadnavirus core antigen further comprises one, two, three, four or five modifications of the group consisting of:
    Δ2=WHcAg/L21A, D26A, L27A, N28A, A29V, V31A substitutions;
    Δ3=WHcAg/N136P, A137P substitutions;

Δ5=WHcAg/replacement of residues 62-85, 65-88 or 64-87 with a heterologous antigen;

Δ6=WHcAg/R150A, R151A, R152A, R156A, R159A, R162A, R163A, R164A, R169A, R170A, R171A, R177A, R178A, R179A, R180A substitutions; and Δ7=WHcAg/N75A, I76A, T77A, S78A, E79A, Q80A, V81A, R82A, T83A substitutions;

wherein the modifications are numbered according to SEQ ID NO:1.

5. The antigenic composition of claim 3, wherein the woodchuck hepadnavirus core antigen comprises the amino acid sequence of SEQ ID NO:13 with a serine at position 61.

6. The antigenic composition of claim 3, wherein the heterologous antigen is a heterologous fusion protein comprising fragments of two, three, four or five different polypeptides.

7. The antigenic composition of claim 3, wherein the heterologous antigen comprises one or more microbial polypeptides.

8. The antigenic composition of claim 7, wherein the heterologous antigen comprises a malarial polypeptide of SEQ ID NO:14.

9. The antigenic composition of claim 8, wherein the woodchuck hepadnavirus core antigen comprises the amino acid sequence of SEQ ID NO:4, and the malarial polypeptide of SEQ ID NO:14 is inserted at position 78 of SEQ ID NO:4.

10. The antigenic composition of claim 3, wherein the hybrid VLP competes with a native, or recombinant soluble form of the heterologous antigen for binding to a heterologous antigen-specific antibody.

11. The antigenic composition of claim 3, wherein the hybrid VLP elicits an antibody response against the heterologous antigen.

12. The antigenic composition of claim 3 wherein the hybrid VLP elicits a measurable neutralizing antibody response against a pathogen comprising the heterologous antigen.

13. A vaccine comprising the antigenic composition of claim 3, and an adjuvant.

14. A method for eliciting a heterologous antigen-reactive antibody response, comprising administering to a mammal an effective amount of the vaccine of claim 13.

15. A method for screening anti-heterologous antigen antibodies comprising:

a) measuring binding of an antibody or fragment thereof to the hybrid woodchuck hepadnavirus core antigen of claim 1;

b) measuring binding of the antibody or fragment thereof to a nonhybrid woodchuck hepadnavirus core antigen devoid of the heterologous antigen; and c) determining that the antibody or fragment thereof is specific for the heterologous antigen when the antibody or fragment thereof binds to the hybrid core antigen but not the nonhyrid core antigen devoid of the heterologous antigen.

16. The antigenic composition of claim 3, wherein the woodchuck hepadnavirus core antigen comprises the amino acid sequence of SEQ ID NO:4.

17. The antigenic composition of claim 3, wherein the woodchuck hepadnavirus core antigen comprises the amino acid sequence of SEQ ID NO:4 with a substitution of an aliphatic amino acid for an arginine at one or more positions selected from the group consisting of 150, 151, 152, 156, 159, 162, 163, 164, 169, 170, 171, 177, 178, 179, and 180, as numbered according to SEQ ID NO:1.

* * * * *